United States Patent [19]

Okamoto et al.

[11] 4,173,630

[45] * Nov. 6, 1979

[54] N²ARYLSULFONYL-L-ARGININAMIDES AND THE PHARMACEUTICALLY ACCEPTABLE SALTS THEREOF

[75] Inventors: Shosuke Okamoto, 15-18, Asahigaoka 3-chome, Tarumi-ku, Kobe-shi, Hyogo; Akiko Hijikata, Kobe; Ryoji Kikumoto, Machida; Yoshikuni Tamao, Yokohama; Kazuo Ohkubo, Machida; Tohru Tezuka, Yokohama; Shinji Tonomura, Tokyo, all of Japan

[73] Assignees: Mitsubishi Chemical Industries Limited, Tokyo; Shosuke Okamoto, Hyogo, both of Japan

[*] Notice: The portion of the term of this patent subsequent to Jul. 19, 1994, has been disclaimed.

[21] Appl. No.: 902,855

[22] Filed: May 4, 1978

Related U.S. Application Data

[60] Continuation-in-part of Ser. No. 760,929, Jan. 19, 1977, Pat. No. 4,101,653, which is a continuation-in-part of Ser. No. 703,704, Jul. 8, 1976, Pat. No. 4,069,323, Ser. No. 671,568, Mar. 29, 1976, Pat. No. 4,049,645, and Ser. No. 671,436, Mar. 29, 1976, Pat. No. 4,062,963, said Ser. No. 671,568, and Ser. No. 671,436, each is a division of Ser. No. 622,390, Oct. 14, 1975, abandoned.

[30] Foreign Application Priority Data

Jun. 6, 1977 [JP] Japan ................................. 52-66508

[51] Int. Cl.² .................... A61K 37/00; C07C 103/52
[52] U.S. Cl. .............................. 424/177; 260/112.5 R
[58] Field of Search ............... 424/267, 177, 244, 258, 424/274, 309, 311, 319, 321; 260/112 SR, 239 A, 239 B, 239 E, 239 BF, 288 R, 288 D, 293.62, 326.1, 326.11, 326.33, 326.5 SF, 347.2, 501.12, 501.14, 518 R, 556 B; 560/10, 251

[56] References Cited

U.S. PATENT DOCUMENTS

| 4,036,955 | 7/1977 | Okamoto et al. | 260/112.5 R |
|---|---|---|---|
| 4,041,156 | 8/1977 | Okamoto et al. | 260/112.5 R |
| 4,046,876 | 9/1977 | Okamoto et al. | 260/112.5 R |
| 4,055,636 | 10/1977 | Okamoto et al. | 260/112.5 R |
| 4,055,651 | 10/1977 | Okamoto et al | 260/112.5 R |
| 4,066,758 | 1/1978 | Okamoto et al. | 260/112.5 R |
| 4,066,759 | 1/1978 | Okamoto et al. | 260/112.5 R |
| 4,069,329 | 1/1978 | Okamoto et al. | 260/112.5 R |
| 4,073,891 | 2/1978 | Okamoto et al. | 260/112.5 R |
| 4,073,892 | 2/1978 | Okamoto et al. | 260/112.5 R |
| 4,073,914 | 2/1978 | Kikumoto et al. | 260/112.5 R |
| 4,073,916 | 2/1978 | Okamoto et al. | 260/112.5 R |

Primary Examiner—Delbert R. Phillips
Attorney, Agent, or Firm—Oblon, Fisher, Spivak, McClelland & Maier

[57] ABSTRACT

N²-arylsulfonyl-L-argininamides and the pharmaceutically acceptable salts thereof have been found to be effective as pharmaceutical agents for the inhibition and suppression of thrombosis in mammals.

15 Claims, No Drawings

N² ARYLSULFONYL-L-ARGININAMIDES AND THE PHARMACEUTICALLY ACCEPTABLE SALTS THEREOF

CROSS-REFERENCE TO RELATED APPLICATIONS

This application is a continuation-in-part of application Ser. No. 760,929 of Jan. 19, 1977 now U.S. Pat. No. 4,101,653, which in turn is a continuation-in-part of the following prior filed applications:

Ser. No. 671,436 of Mar. 29, 1976-U.S. Pat. No. 4,062,963

Ser. No. 671,568 of Mar. 29, 1976-U.S. Pat. No. 4,049,645

Ser. No. 703,704 of Jul. 8, 1976-U.S. Pat. No. 4,069,323

Applications Ser. Nos. 671,436 and 671,568 are divisional applications of Ser. No. 622,390 filed Oct. 14, 1975, now abandoned.

BACKGROUND OF THE INVENTION

1. Field of the Invention

This invention relates to the discovery of certain new and useful N²-arylsulfonyl-L-argininamides and the pharmaceutically acceptable salts thereof, which are of special value in view of their outstanding antithrombotic properties and low toxicities.

2. Description of the Prior Art

In the past, there have been many attempts to obtain new and improved agents for the treatment of thrombosis. The N²-(p-tolylsulfonyl)-L-arginine esters have been found to be one type of agent which can be used and these have been found to be effective in dissolving blood clots. (U.S. Pat. No. 3,622,615, issued Nov. 23, 1971). One family of compounds which have been found to be particularly useful as highly specific inhibitors of thrombin for the control of thrombosis is the N²-dansyl-L-arginine ester or amide. (Our pending U.S. application Ser. No. 496,939, filed Aug. 13, 1974 now U.S. Pat. No. 3,978,045). However, there is a continuing need for a highly specific inhibitor of thrombin for the control of thrombosis, which exhibits lower toxicity.

SUMMARY OF THE INVENTION

It has now been discovered that N²-arylsulfonyl-L-argininamides exhibit antithrombotic activity and even lower toxicity levels at the same relative potencies, as compared with the N²-dansyl-L-arginine ester or amide.

The present invention provides an N²-arylsulfonyl-L-argininamide having the formula:

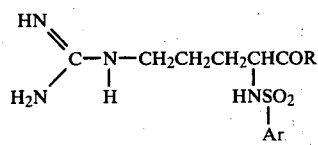

and the pharmaceutically acceptable salt thereof, wherein R is selected from the group consisting of

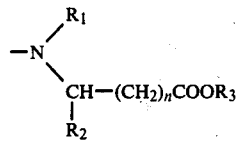

wherein $R_1$ is selected from the group consisting of hydrogen, $C_1$-$C_{10}$ alkyl, $C_3$-$C_{10}$ alkenyl, $C_3$-$C_{10}$ alkynyl, $C_2$-$C_{10}$ alkoxy-alkyl, $C_2$-$C_{10}$ alkylthioalkyl, $C_2$-$C_{10}$ alkylsulfinylalkyl, $C_1$-$C_{10}$ hydroxyalkyl, $C_2$-$C_{10}$ carboxyalkyl, $C_3$-$C_{10}$ alkoxycarbonylalkyl, $C_3$-$C_{10}$ alkylcarbonylalkyl, $C_1$-$C_{10}$ haloalkyl, $C_7$-$C_{15}$ aralkyl, $C_8$-$C_{15}$ α-carboxyaralkyl, $C_3$-$C_{10}$ cycloalkyl, $C_4$-$C_{10}$ cycloalkylalkyl, furfuryl, tetrahydrofurfuryl optionally substituted with at least one $C_1$-$C_5$ alkyl, $C_1$-$C_5$ alkoxy or mixtures thereof, 3-furylmethyl, tetrahydro-3furylmethyl optionally substituted with at least one $C_1$-$C_5$ alkyl, $C_1$-$C_5$ alkoxy or mixtures thereof, tetrahydro-2-pyranylmethyl optionally substituted with at least one $C_1$-$C_5$ alkyl, $C_1$-$C_5$ alkoxy or mixtures thereof, 1,4-dioxa-2-cyclohexylmethyl optionally substituted with at least one $C_1$-$C_5$ alkyl, $C_1$-$C_5$ alkoxy or mixtures thereof, 2-thenyl, 3-thenyl, tetrahydro-2-thenyl optionally substituted with at least one $C_1$-$C_5$ alkyl, $C_1$-$C_5$ alkoxy or mixtures thereof, and tetrahydro-3-thenyl; $R_2$ is selected from the group consisting of hydrogen, $C_1$-$C_{10}$ alkyl, carboxy, $C_2$-$C_{10}$ alkoxycarbonyl, phenyl optionally substituted with at least one $C_1$-$C_5$ alkyl, $C_1$-$C_5$ alkoxy or mixtures thereof, $C_7$-$C_{12}$ aralkyl and ring substituted benzyl wherein said substituent is $C_1$-$C_5$ alkyl or $C_1$-$C_5$ alkoxy; $R_3$ is selected from the group consisting of hydrogen, $C_1$-$C_{10}$ alkyl, $C_6$-$C_{10}$ aryl, $C_7$-$C_{12}$ aralkyl and 5-indanyl; and n is an integer of 0, 1 or 2

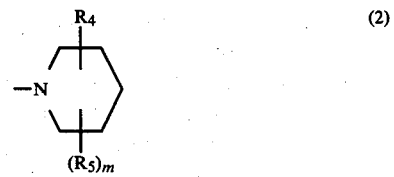

wherein $R_4$ is —$COOR_6$ wherein $R_6$ is selected from the group consisting of hydrogen, $C_1$-$C_{10}$ alkyl, $C_6$-$C_{10}$ aryl, $C_7$-$C_{12}$ aralkyl and 5-indanyl; each $R_5$ independently is hydrogen, $C_1$-$C_{10}$ alkyl, phenyl, $C_1$-$C_5$ alkoxy or carboxy; m is an integer of 1 to 5; $R_4$ is substituted at the 2 or 3-position; and $R_5$ can be substituted at the 2, 3, 4, 5 or 6-position,

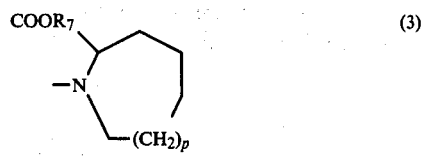

optionally substituted with at least one $C_1$-$C_5$ alkyl, $C_1$-$C_5$ alkoxy or mixtures thereof, wherein $R_7$ is selected from the group consisting of hydrogen, $C_1$-$C_{10}$ alkyl, $C_6$-$C_{10}$ aryl, $C_7$-$C_{12}$ aralkyl and 5-indanyl; and p is an integer of 1, 2, 3 or 4,

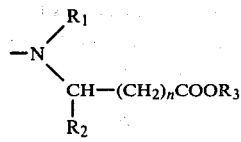

$R_1$ is selected from the group consisting of hydrogen, $C_1$-$C_{10}$ alkyl, such as methyl, ethyl, propyl, butyl, isobutyl, pentyl, hexyl, octyl, decyl or the like, alkenyl of 3-10 (preferably 3-6) carbon atoms, such as allyl, 2-butenyl, 3-butenyl, 2-pentenyl or the like, alkynyl of 3-10 (preferably 3-6) carbon atoms, such as 2-propynyl, 2-butynyl, 3-butynyl or the like, alkoxyalkyl of 2-10 (preferably 2-6) carbon atoms, such as methoxymethyl, ethoxymethyl, propoxymethyl, 2-methoxyethyl, 2-ethoxyethyl, 2-propoxyethyl, 2-methoxypropyl, 3-methoxypropyl, 3-ethoxypropyl, 3-propoxypropyl, 4-methoxybutyl, 4-ethoxybutyl, 4-butoxybutyl, 5-butoxypentyl or the like, alkylthioalkyl of 2-10 (preferably 2-6) carbon atoms, such as methylthiomethyl, ethylthiomethyl, propylthiomethyl, 2-methylthioethyl, 2-ethylthioethyl, 2-propylthioethyl, 3-methylthiopropyl, 2-methylthiopropyl, 3-ethylthiopropyl, 3-propylthiopropyl, 4-methylthiobutyl, 4-ethylthiobutyl, 4-butylthiobutyl, 5-butylthiopentyl or the like, alkylsulfinylalkyl of 2-10 (preferably 2-6) carbon atoms, such as methylsulfinylmethyl, ethylsulfinylmethyl, propylsulfinylmethyl, 2-methylsulfinylethyl, 2-ethylsulfinylethyl, 2-propylsulfinylethyl, 3-methylsulfinylpropyl, 3-ethylsulfinylpropyl or the like, hydroxyalkyl of 1-10 (preferably 1-6) carbon atoms, such as hydroxymethyl, 2-hydroxyethyl, 3-hydroxypropyl, 2-hydroxypropyl, 4-hydroxybutyl, 3-hydroxybutyl, 5-hydroxypentyl or the like, carboxyalkyl of 2-10 (preferably 2-7) carbon atoms, such as carboxymethyl, 2-carboxyethyl, 2-carboxypropyl, 3-carboxypropyl, 1-carboxybutyl, 2-carboxybutyl, 4-carboxybutyl or the like, alkoxycarbonylalkyl of 3-10 (preferably 3-8) carbon atoms, such as methoxycarbonylmethyl, 2-methoxycarbonylethyl, 2-ethoxycarbonylpropyl, 3-methoxycarbonylpropyl, 1-methoxycarbonylbutyl, 2-ethoxycarbonylbutyl, 4-methoxycarbonylbutyl or the like, alkylcarbonylalkyl of 3-10 (preferably 3-8) carbon atoms such as methylcarbonylethyl, haloalkyl of 1-10 (preferably 1-5) carbon atoms such as chloromethyl, 2-chloroethyl, 2-bromoethyl, 2-chloropropyl, 3-chloropropyl, 2-chlorobutyl, 4-chlorobutyl or the like, aralkyl of 7-15 (preferably 7-10) carbon atoms, such as benzyl, phenethyl, 3-phenylpropyl, 4-phenylbutyl, 6-phenylhexyl, 1-phenylethyl, 2-phenylpropyl or the like, α-carboxyaralkyl of 8-15 (preferably 8-12) carbon atoms, such as α-carboxybenzyl, α-carboxyphenethyl or the like, $C_3$-$C_{10}$ cycloalkyl, such as cyclopropyl, cyclobutyl, cyclopentyl, cyclohexyl, cycloheptyl, cyclooctyl, cyclononyl or cyclodecyl, $C_4$-$C_{10}$ cycloalkylalkyl, such as cyclopropylmethyl, cyclopentylmethyl, cyclohexylmethyl, 2-cyclohexylethyl, cyclooctylmethyl or the like, furfuryl, tetrahydrofurfuryl optionally substituted with one or more $C_1$-$C_5$ alkyl and/or $C_1$-$C_5$ alkoxy groups, 3-furylmethyl, tetrahydro-3-furylmethyl optionally substituted with one or more $C_1$-$C_5$ alkyl and/or $C_1$-$C_5$ alkoxy groups, tetrahydro-2-pyranylmethyl optionally substituted with one or more $C_1$-$C_5$ alkyl and/or $C_1$-$C_5$ alkoxy groups, 1,4-dioxa-2-cyclohexylmethyl optionally substituted with one or more $C_1$-$C_5$ alkyl and/or $C_1$-$C_5$ alkoxy groups, 2-thenyl, 3-thenyl, tetrahydro-2-thenyl optionally substituted

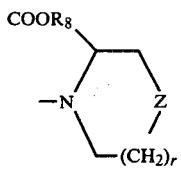

wherein $R_8$ is selected from the group consisting of hydrogen, $C_1$-$C_{10}$ alkyl, $C_6$-$C_{10}$ aryl, $C_7$-$C_{12}$ aralkyl and 5-indanyl; Z is selected from the group consisting of oxy, thio and sulfinyl; and r is an integer of 0 or 1, and

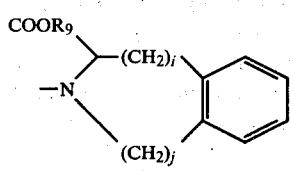

wherein $R_9$ is selected from the group consisting of hydrogen, $C_1$-$C_{10}$ alkyl, $C_6$-$C_{10}$ aryl, $C_7$-$C_{12}$ aralkyl and 5-indanyl; i is an integer of 0, 1 or 2; j is an integer of 0, 1 or 2; and the sum of i+j is an integer of 1 or 2; and Ar is a phenyl group substituted with at least one substituent selected from the group consisting of alkyl, alkoxy and alkylcarbonyl, said substituent being optionally substituted with halo, alkoxy or alkoxycarbonyl, the number of the carbon atoms of each substituent which is attached to the phenyl group being 3 to 7 and the said phenyl group being optionally substituted further with at least one substituent selected from the group consisting of methyl, ethyl, methoxy, ethoxy, hydroxyl and halo.

The pharmaceutically acceptable salts thereof are also included within the scope of this invention. This invention also relates to an anticoagulant containing an $N^2$-arylsulfonyl-L-argininamide or the pharmaceutically acceptable salt thereof.

Furthermore, this invention relates to a method for inhibiting activity and suppressing activation of thrombin in vivo in mammals which comprises administering to a mammal a pharmaceutically antithrombotically effective amount of an $N^2$-arylsulfonyl-L-argininamide or the pharmaceutically acceptable salts thereof.

DETAILED DESCRIPTION OF THE PREFERRED EMBODIMENTS

This invention relates to a group of $N^2$-arylsulfonyl-L-argininamides of the formula (I):

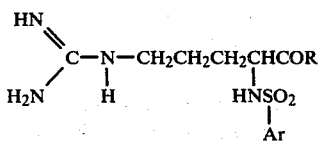

Illustrative of R are the following:
In the case where R is with one or more $C_1$–$C_5$ alkyl and/or $C_1$–$C_5$ alkoxy groups and tetrahydro-3-thenyl; $R_2$ is selected from the group consisting of hydrogen, alkyl of 1–10 (preferably 1–5) carbon atoms, such as methyl, ethyl, propyl, isopropyl, butyl, isobutyl, sec-butyl, pentyl or the like, carboxy, alkoxycarbonyl of 2–10 (preferably 2–5) carbon atoms, such as methoxycarbonyl, ethoxycarbonyl, propoxycarbonyl or the like, phenyl optionally substituted with one or more $C_1$–$C_5$ alkyl and/or $C_1$–$C_5$ alkoxy groups, aralkyl of 7–12 (preferably 7–10) carbon atoms, such as benzyl, phenethyl or the like, and ring substituted benzyl wherein said substituent is alkyl of 1–5 (preferably 1–3) carbon atoms, such as methyl, ethyl, propyl or isopropyl, or alkoxy of 1–5 (preferably 1–3) carbon atoms, such as methoxy, ethoxy, propoxy or isopropoxy; $R_3$ is selected from the group consisting of hydrogen, $C_1$–$C_{10}$ alkyl, such as methyl, ethyl, propyl, butyl, tert-butyl, hexyl, oxtyl, decyl or the like, $C_6$–$C_{10}$ aryl, such as phenyl, m-tolyl, naphthyl or the like, aralkyl of 7–12 (preferably 7–10) carbon atoms, such as benzyl, phenethyl or the like, and 5-indanyl; and n is an integer of 0, 1 or 2.

In the case wherein R is

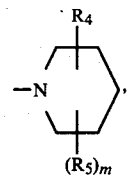     (2)

$R_4$ is —COOR$_6$ wherein $R_6$ is selected from the group consisting of hydrogen, $C_1$–$C_{10}$ alkyl, such as methyl, ethyl, propyl, butyl, tert-butyl, hexyl, octyl, decyl or the like, $C_6$–$C_{10}$ aryl, such as phenyl, m-tolyl, naphthyl or the like, aralkyl of 7–12 (preferably 7–10) carbon atoms, such as benzyl, phenethyl or the like, and 5-indanyl; each $R_5$ independently is hydrogen, alkyl of 1–10 (preferably 1–6) carbon atoms, such as methyl, ethyl, propyl, isopropyl, butyl, hexyl, octyl, decyl or the like, phenyl, $C_1$–$C_5$ alkoxy or carboxy; m is an integer of 1 to 5; $R_4$ is substituted at the 2 or 3-position; and $R_5$ can be substituted at the 2, 3, 4, 5 or 6-position.

In the case where R is

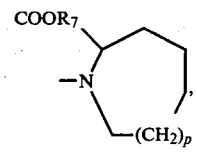     (3)

$R_7$ is selected from the group consisting of hydrogen, $C_1$–$C_{10}$ alkyl, such as methyl, ethyl, propyl, butyl, tert-butyl, hexyl, oxtyl, decyl or the like, $C_6$–$C_{10}$ aryl, such as phenyl, m-tolyl, naphthyl or the like, aralkyl of 7–12 (preferably 7–10) carbon atoms, such as benzyl, phenethyl or the like, and 5-indanyl; and p is an integer of 1, 2, 3 or 4, and the ring being optionally substituted with one or more $C_1$–$C_5$ alkyl and/or $C_1$–$C_5$ alkoxy groups.

In the case where R is

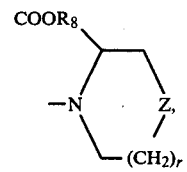     (4)

$R_8$ is selected from the group consisting of hydrogen, $C_1$–$C_{10}$ alkyl, such as methyl, ethyl, propyl, butyl, tert-butyl, hexyl, octyl, decyl or the like, $C_6$–$C_{10}$ aryl, such as phenyl, m-tolyl, naphthyl or the like, aralkyl of 7–12 (preferably 7–10) carbon atoms, such as benzyl, phenethyl or the like, and 5-indanyl; Z is selected from the group consisting of oxy (—O—), thio (—S—) and sulfinyl (—SO—); r is an integer of 0 or 1.

In the case where R is

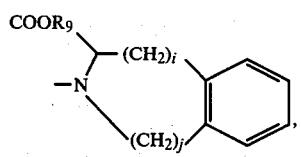     (5)

wherein $R_9$ is selected from the group consisting of hydrogen, $C_1$–$C_{10}$ alkyl, such as methyl, ethyl, propyl, butyl, tert-butyl, hexyl, octyl, decyl or the like, $C_6$–$C_{10}$ aryl, such as phenyl, m-tolyl, naphthyl or the like, aralkyl or 7–12 (preferably 7–10) carbon atoms, such as benzyl, phenethyl or the like, and 5-indanyl; i is an integer of 0, 1 or 2; j is an integer of 0, 1 or 2; and the sum of i+j is an integer of 1 or 2.

Suitable illustrations of R include

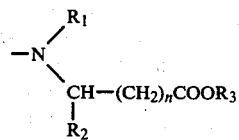     (1)

wherein $R_1$ is $C_1$–$C_{10}$ alkyl, $C_2$–$C_{10}$ alkoxyalkyl, $C_7$–$C_{15}$ aralkyl, $C_3$–$C_{10}$ cycloalkyl, $C_4$–$C_{10}$ cycloalkylalkyl or tetrahydrofurfuryl optionally substituted with one or more $C_1$–$C_5$ alkyl and/or $C_1$–$C_5$ alkoxy; $R_2$ is hydrogen or $C_1$–$C_{10}$ alkyl; and n is an integer of 0, 1 or 2,

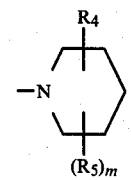     (2)

wherein $R_4$ is —COOR$_6$ wherein $R_6$ is hydrogen, $C_1$–$C_{10}$ alkyl, $C_6$–$C_{10}$ aryl, $C_7$–$C_{12}$ aralkyl or 5-indanyl; $R_5$ independently is hydrogen or $C_1$–$C_{10}$ alkyl; m is an integer of 1 or 2; $R_4$ is substituted at the 2-position; and $R_5$ can be substituted at the 2, 3, 4, 5 or 6-position,

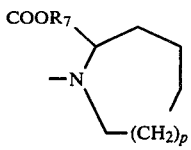

(3)

wherein $R_7$ is hydrogen, $C_1$–$C_{10}$ alkyl, $C_6$–$C_{10}$ aryl, $C_7$–$C_{12}$ aralkyl or 5-indanyl; p is an integer of 1, 2, 3 or 4; and the above alkyleneiminyl group being optionally substituted with one or more $C_1$–$C_5$ alkyl and/or $C_1$–$C_5$ alkoxy, or

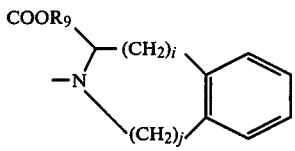

(4)

wherein $R_9$ is hydrogen, $C_1$–$C_{10}$ alkyl, $C_6$–$C_{10}$ aryl, $C_7$–$C_{12}$ aralkyl or 5-indanyl; i is an integer of 0, 1 or 2; j is an integer of 0, 1 or 2; and the sum of i+j is an integer of 1 or 2.

Illustrations of substituents of the phenyl group in Ar include alkyl such as propyl, butyl, isobutyl, sec-butyl, t-butyl, pentyl, hexyl, heptyl and the like; alkoxy such as propoxy, isopropoxy, butoxy, isobutoxy, tert-butoxy, pentyloxy, isopentyloxy, hexyloxy, heptyloxy and the like; alkylcarbonyl such as propionyl, butyryl, valeryl, hexanoyl and the like; haloalkyl such as 3-chloropropyl, 3-bromopropyl, 3-chlorobutyl, 4-chlorobutyl, 4-bromobutyl, 5-chloropentyl, 5-bromopentyl and the like; haloalkoxy such as 3-chloropropoxy, 3-bromopropoxy, 3-chlorobutoxy, 4-chlorobutoxy, 4-bromobutoxy, 5-chloropentyloxy, 5-bromopentyloxy and the like; haloalkylcarbonyl such as 2-chloropropionyl, 3-bromopropionyl, 4-chlorobutyryl, 4-bromobutyryl, 5-chlorovaleryl, 4-chlorovaleryl, 5-bromovaleryl and the like; alkoxyalkyl such as ethoxymethyl, propoxymethyl, butyoxymethyl, 2-methoxyethyl, 2-ethoxyethyl, 2-propoxyethyl, 3-methoxypropyl, 3-ethoxypropyl, 3-methoxybutyl, 4-methoxybutyl and the like; alkoxyalkoxy such as ethoxymethoxy, propoxymethoxy, butoxymethoxy, 2-methoxyethoxy, 2-ethoxyethoxy, 2-propoxyethoxy, 3-methoxypropoxy, 3-ethoxypropoxy, 3-methoxybutoxy, 4-methoxybutoxy and the like; alkoxyakylcarbonyl such as 2-methoxyacetyl, 2-ethoxyacetyl, 2-propoxyacetyl, 3-methoxypropionyl, 3-ethoxypropionyl, 4-methoxybutyryl, 4-methoxyvaleryl and the like; alkoxycarbonylalkyl such as methoxycarbonylmethyl, ethoxycarbonylmethyl, propoxycarbonylmethyl, 2-methoxycarbonylethyl, 2-ethoxycarbonylethyl, 3-methoxycarbonylpropyl and the like; alkoxycarbonylalkoxy such as methoxycarbonylmethoxy, ethoxycarbonylmethoxy, propoxycarbonylmethoxy, 2-methoxycarbonylethoxy, 2-ethoxycarbonylethoxy, 3-methoxycarbonylpropoxy and the like; alkoxycarbonylalkylcarbonyl such as 2-methoxycarbonylacetyl, 2-ethoxycarbonylacetyl, 3-methoxycarbonylpropionyl and the like. The number of the carbon atoms in the above substituents of the phenyl group is in the range of 3–7 (preferably 3–5).

Illustrations of Ar include 3-propyl-4-methoxyphenyl, 3-tert-butyl-4-methoxyphenyl, 3-sec-butyl-4-hydroxyphenyl, 3-propoxyphenyl, 3-methoxy-4-propoxyphenyl, 3-propoxy-4-methoxyphenyl, 2,4-dimethoxy-3-propoxyphenyl, 3-butoxyphenyl, 2-butoxyphenyl, 2,5-dibutoxyphenyl, 3,4-dibutoxyphenyl, 2,4-dibutoxyphenyl, 3-methyl-4-butoxyphenyl, 3,5-dimethyl-4-butoxyphenyl, 2,4-dimethoxy-3-butoxyphenyl, 2,4-dichloro-3-butoxyphenyl, 3-pentyloxyphenyl, 3-isopentyloxyphenyl, 3,5-dimethyl-4-pentyloxyphenyl, 2,4-dimethoxy-3-pentyloxyphenyl, 2,4-dimethoxy-3-hexyloxyphenyl, 2,4-dimethoxy-3-(3-bromopropoxy)phenyl, 2,4-dimethoxy-3-(2-methoxyethoxy)phenyl, 2,4-dimethoxy-3-(2-ethoxyethoxy)phenyl, 3-methyl-4-(2-methoxyethoxy)phenyl, 3-methyl-4-(3-methoxypropoxy)phenyl, 3-valeryl-4-methoxyphenyl, 2,4-dimethoxy-4-(3-methoxycarbonylpropoxy)phenyl and the like.

Illustrative of $N^2$-arylsulfonyl-L-argininamides of the compounds of this invention are:

1-[$N^2$-(3-butoxyphenylsulfonyl)-L-arginyl]-4-methyl-2-piperidinecarboxylic acid $N^2$-(3-butoxyphenylsulfonyl)-L-arginyl-N-tetrahydrofurfuylglycine 1-[$N^2$-(3-isobutoxyphenylsulfonyl)-L-arginyl]-4-ethyl-2-piperidinecarboxylic acid 1-[$N^2$-(3-tert-butyl-4-methoxyphenylsulfonyl)-L-arginyl]-4-methyl-2-piperidinecarboxylic acid 1-[$N^2$-(2,4-dimethoxy-3-butoxyphenylsulfonyl)-L-arginyl]-4-methyl-2-piperidinecarboxylic acid 1[$N^2$-(2,4-dimethoxy-3-propoxyphenylsulfonyl)-L-arginyl]-4-methyl-2-piperidinecarboxylic acid Ethyl 1-[$N^2$-(2,4-dimethoxy-3-butoxyphenylsulfonyl)-L-arginyl]-4-methyl-2-piperidinecarboxylate $N^2$-(2,4-dimethoxy-3-butoxyphenylsulfonyl)-L-arginyl-N-(2-methoxyethyl)glycine 1[$N^2$-(3-valeryl-4-methoxyphenylsulfonyl)-L-arginyl]-4-methyl-2-piperidinecarboxylic acid 1-[$N^2$-(3,5-dimethyl-4-butoxyphenylsulfonyl)-L-arginyl]-4-methyl-2-piperidinecarboxylic acid The pharmaceutically acceptable salts of the above compounds are of course also included within the scope of this invention.

As one skilled in the art can readily appreciate, the carbon atom of the $N^2$-arylsulfonyl-L-argininamides, to which the carboxyl group or the ester thereof is attached can be an asymmetric carbon atom allowing for the existence of two optionally active isomers, the D- and L-diastereoisomers, as well as the racemate, DL-mixture.

In accordance with findings concerning the antithrombotic activity of such compounds possessing an asymmetric carbon atom, the compounds of the present invention having the D-configuration are more active than those of the L-configuration and are the preferred compounds, although the L- and DL-forms of the instant compounds are also considered within the purview of the present invention. The above compounds are intended only to illustrate the variety of structures which can be used in the process of this invention, and the above listing is not to be construed as limiting the scope of the invention. For the preparation of the compounds of this invention, various methods can be employed depending upon the particular starting materials and/or intermediates involved. Successful preparation of these compounds is possible by way of several synthetic routes which are outlined below.

(a) Condensation of an L-argininamide with an arylsulfonyl halide

This process may be illustrated as follows:

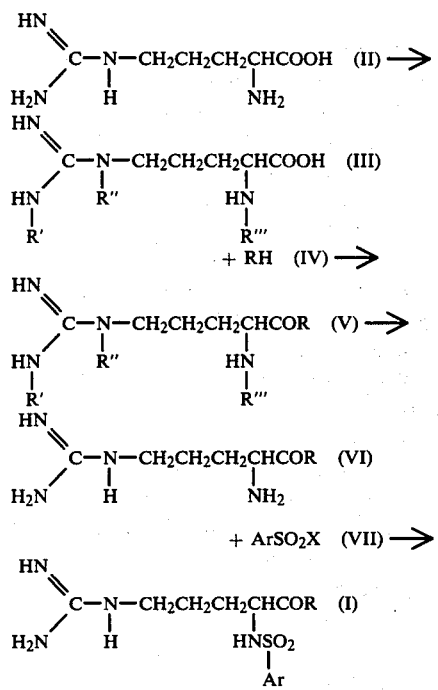

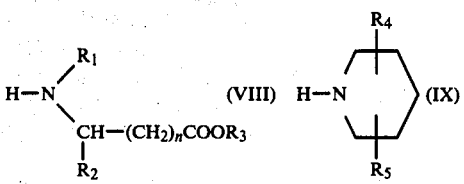

In the above formulas, R and Ar are as defined herein aboe; X is halogen; R''' is a protective group for the α-amino group, such as benzyloxycarbonyl or tert-butoxycarbonyl; R' and R'' are selected from the group consisting of hydrogen and protective groups for the guanidino group, such as nitro, tosyl, trityl, oxycarbonyl and the like; and at least one of R' and R'' is a protective group for the guanidino group.

The $N^2$-arylsulfonyl-L-argininamide (I) is prepared by the condensation of an L-argininamide (VI) with a substantially equimolar amount of an arylsulfonyl halide (VII), preferably a chloride.

The condensation reaction is generally effected in a suitable reaction-inert solvent in the presence of an excess of a base, such as an organic base (triethylamine, pyridine) or a solution of an inorganic base (sodium hydroxide, potassium carbonate), at a temperature of 0° C. to the boiling temperature of the solvent for a period of 10 minutes to 15 hours.

The preferred solvents for the condensation include benzene-diethyl ether, diethyl ether-water and dioxane-water.

After the reaction is complete, the formed salt is extracted with water, and the solvent is removed by such standard means as evaporation under reduced pressure to give the $N^2$-arylsulfonyl-L-argininamide (I), which can be purified by trituration or recrystallization from a suitable solvent, such as diethyl ether-tetrahydrofuran, diethyl ether-methanol and water-methanol, or may be chromatographed on silica gel. The L-argininamides (VI) starting materials required for the condensation reaction can be prepared by protecting the guanidino and α-amino groups of L-arginine (II) via nitration, acetylation, formylation, phthaloylation, trifluoroacetylation, p-methoxybenzyloxycarbonylation, benzoylation, benzyloxycarbonylation, tert-butoxycarbonylation or tritylation and then condensing the formed $N^G$-substituted-$N^2$-substituted-L-arginine (III) with a corresponding amino acid derivative (IV) by such a conventional process as the acid chloride method, azide method, mixed anhydride method, activated ester method or carbodiimide method, and thereafter selectively removing the protective groups from the formed $N^G$-substituted-$N^2$-substituted-L-argininamide (V).

The amino acid derivatives (IV) which are the starting materials for the preparation of the $N^G$-substituted-$N^2$-substituted-L-argininamides (V) are represented by the following formulas:

$$H-N\begin{matrix}R_1\\ \\CH-(CH_2)_nCOOR_3\\ \\R_2\end{matrix} \quad (VIII) \qquad H-N\begin{matrix}R_4\\ \\ \\R_5\end{matrix} \quad (IX)$$

In the above formulas, $R_1, R_2, R_3, R_4, R_5, R_7, R_8, R_9$, Z, n, p, r, i, and j are as defined herein above. The amino acid derivatives of the above formula (VIII) can be prepared by the condensation of a haloacetate, 3-halopropionate or 4-halobutyrate with an appropriate amine having the formula $R_1NH_2$. (See, J. Org. Chem., 25 728–732 (1960)).

The condensation reaction is generally carried out without a solvent or in a solvent, such as benzene or ether, in the presence of an organic base, such as triethylamine or pyridine, at a temperature of 0° C. to 80° C. for a period of 10 minutes to 20 hours. After the reaction is complete, the formed amino acid derivative is separated by such conventional means as extraction with a suitable solvent or evaporation of the reaction solvent and thereafter purified by distillation under reduced pressure.

Among the amino acid derivative, amino acid tert-butyl ester derivatives are preferred, because they are easily converted to other ester derivatives by acidolysis in the presence of a corresponding alcohol employing an inorganic acid (HCl, $H_2SO_4$, etc.) or an organic acid (toluenesulfonic acid, trifluoroacetic acid, etc.). In accordance with the process employed for preparing 2-piperidinecarboxylic acid derivatives (IX), the following scheme is illustrative:

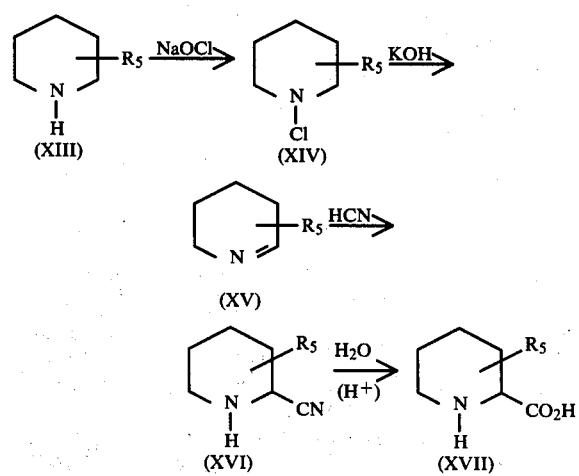

In the first reaction of the aforementioned scheme, an appropriately substituted piperidine (XIII) is contacted with an aqueous sodium hypochlorite solution at a temperature of −5° C. to 0° C. The resultant product (XIV)

is isolated by extraction with a solvent, e.g., diethyl ether, and then treated with potassium hydroxide in a lower alkanol solvent to give the 1,2-dehydropiperidine (XV). The action of cyanogenating agents, e.g., hydrogen cyanide or sodium cyanide converts the 1,2-dehydropiperidines (XV) to the corresponding 2-cyano analogs (XVI). Hydrolysis of the 2-cyanopiperidines (XVI) to yield the 2-piperidinecarboxylic acids (XVII) is effected by treatment of the 2-cyanopiperidines (XVI) with an inorganic acid, such as hydrochloric acid or sulfuric acid. The arylsulfonyl halides (VII) which are the starting materials for the preparation of the $N^2$-arylsulfonyl-L-argininamides (I) can be prepared by halogenating the requisite arylsulfonic acids or their salts, e.g., sodium salts, by conventional methods well known to those skilled in the art.

In practice, halogenation is carried out without a solvent or in a suitable solvent e.g., halogenated hydrocarbons or DMF in the presence of a halogenating agent, e.g., phosporous oxychloride, thionyl chloride, phosphorous trichloride, phosphorous tribromide or phosphorous pentachloride, at a temperature of $-10°$ C. to 200° C. for a period of 5 minutes to 5 hours. After the reaction is complete, the reaction product is poured into ice water and then extracted with a solvent such as ether, benzene, ethyl acetate, chloroform or the like.

The arylsulfonyl halide can be purified by recrystallization from a suitable solvent such as hexane, benzene or the like.

(b) Removal of the $N^G$-substituent from an $N^G$-substituted-$N^2$-arylsulfonyl-L-argininamide This process may be illustrated as follows:

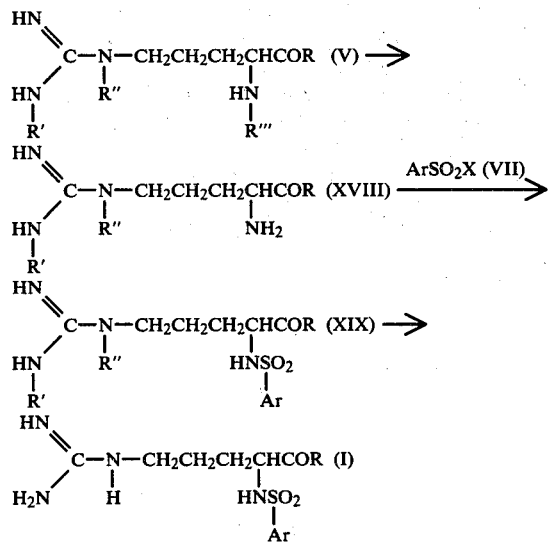

In the above formulas, R, Ar, X, R', R" and R''' are as defined herein above.

The $N^2$-arylsulfonyl-L-argininamide (I) is prepared by removing the $N^G$-substituent from an $N^G$-substituted-$N_2$-arylsulfonyl-L-argininamide (XIX) by means of acidolysis or hydrogenolysis.

The acidolysis is generally effected by contacting the $N^G$-substituted-$N^2$-arylsulfonyl-L-argininamide (XIX) and an xcess of an acid such as hydrogen fluoride, hydrogen chloride, hydrogen bromide or trifluoroacetic acid, without a solvent or in a solvent, such as an ether (tetrahydrofuran, dioxane), an alcohol (methanol, ethanol) or acetic acid at a temperature of $-10°$ C. to 100° C., and preferably at room temperature for a period of 30 minutes to 24 hours.

The products are isolated by evaporation of the solvent and the excess acid, or by trituration with a suitable solvent followed by filtration and drying.

Because of the use of the excess acid, the products are generally the acid addition salts of the $N^2$-arylsulfonyl-L-argininamides (I), which can be easily converted to a free amide by neutralization.

The removal of the nitro group and the oxycarbonyl group, e.g., benzyloxycarbonyl, p-nitrobenzyloxycarbonyl, is readily accomplished by the hydrogenolysis.

At the same time, the benzyl ester moiety which can be included in the R group is converted to the carboxyl group by the hydrogenolysis.

The hydrogenolysis is effected in a reaction-inert solvent, e.g., alcohols (methanol, ethanol), or ethers (tetrahydrofuran, dioxane), in the presence of a hydrogen-activating catalyst, e.g., Raney nickel, palladium, or platinum, in a hydrogen atmosphere at a temperature of 0° C. to the boiling temperature of the solvent for a period of 2 hours to 120 hours.

The hydrogen pressure is not critical, and atmospheric pressure is sufficient.

The $N^2$-arylsulfonyl-L-argininamides (I) are isolated by filtration of the catalyst followed by evaporation of the solvent.

The $N^2$-arylsulfonyl-L-argininamides can be purified in the same manner as described above.

The $N^G$-substituted-$N^2$-arylsulfonyl-L-argininamides (XIX) starting materials can be prepared by condensing an $N^G$-substituted-$N^2$-substituted-L-arginine (III) (generally tne $N^G$-substituent is nitro or acyl, and the $N^2$-substituent is a protective group for the amino group, such as benzyloxycarbonyl, tert-butoxycarbonyl, or the like) and a corresponding amino acid derivative (IV), selectively removing only the $N^2$-substituent of an $N^G$-substituted-$N^2$-substitued L-argininamide (V) by means of catalytic hydrogenolysis or acidolysis, and then condensing the thus obtained $N^G$-substituted-L-argininamide (XVIII) with an arylsulfonyl halide (VII), preferably a chloride in the presence of a base in a solvent. These reaction conditions are as described above in the condensation of an L-argininamide with an arylsulfonyl halide, and the removal of the $N^G$-substituent from an $N^G$-substituted-$N^2$-arylsulfonyl-L-argininamide.

(c) Condensation of an $N^2$-arylsulfonyl-L-arginyl halide with an amino acid derivative This process may be illustrated as follows:

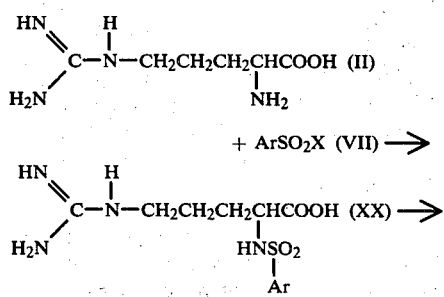

-continued

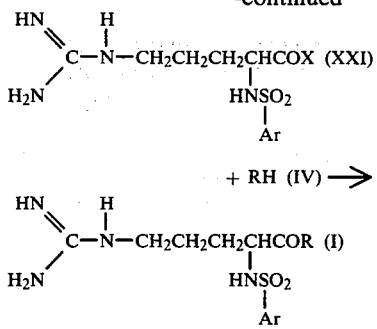

In the above formulas, R, Ar and X are as defined herein above.

The N²-aruylsulfonyl-L-argininamide (I) is prepared by th condensation of an N²-arylsulfonyl-L-arginyl halide (XXI), preferably a chloride with at least an equimolar amount of an amino acid derivative (IV).

The condensation reaction can be carried out without an added solvent in the presence of a base. However, satisfactory results will be obtained with the use of a solvent such as basic solvents (dimethylformamide, dimethylacetaminde, etc.) or halogenated solvents (chloroform, dichloromethane, etc.).

The amount of the solvent to be used is not critical and may vary from about 5 to 100 times the weight of the N²-arylsulfonyl-L-arginyl halide (XXI).

Preferred condensation reaction temperatures are in the range of from $-10°$ C. to room temperature. The reaction time is not critical, but varies with the amino acid derivative (IV) employed. In general, a period of from 5 minutes to 10 hours is operable.

The obtained N²-arylsulfonyl-L-argininamide can be isolated and purified in the same manner as described above. The N²-arylsulfonyl-L-arginyl halide (XXI) starting materials required for the condensation reaction can be prepared by reacting an N²-arylsulfonyl-L-arginine (XX) with at least an equimolar amount of a halogenating agent such as thionyl chloride, phosphorous oxychloride, phosphorus trichloride, phosphorous pentachloride or phosphorus tribromide. Teh halogenation can be carried out with or without an added solvent.

The preferred solvents are chlorinated hydrocarbons such as chloroform and dichloromethane, and ethers such as tetrahydrofuran and dioxane.

The amount of the solvent to be used is not critical and may vary from about 5 to 100 times the weight of the N²-arylsulfonyl-L-arginine (XX).

Preferred reaction temperature are in the range of $-10°$ C. to room temperature. The reaction time is not critical, but varies with the halogenating agent and reaction temperature. In general, a period of 15 minutes to 5 hours is operable.

The N²-arylsulfonyl-L-arginines (XX) which are the starting materials for the preparation of the N²-arylsulfonyl-L-arginyl halides (XXI) can be prepared by the condensation of L-arginine (II) with a substantially equimolar amount of arylsulfonyl halides (VII), by a method similar to that described in the condensation of an L-argininamide with an arylsulfonyl halide.

It is well recognized in the art that an ester derivative of te N²-arylsulfonyl-L-argininamide (I) wherein $R_3$, $R_6$, $R_7$, $R_8$ or $R_9$ is alkyl, aralkyl, aryl or 5-indanyl, can be prepared from a carboxylic acid derivative of the N²-arylsulfonyl-L-argininamide wherein $R_3$, $R_6$, $R_7$, $R_8$ or $R_9$ is hydrogen, by the conventional esterification methods well known to those skilled in the art.

It is also well recognized in the art that the carboxylic acid derivative can be prepared from the ester derivative by the conventional hydrolysis or acidolysis methods. The conditions under which esterification, hydrolysis or acidolysis would be carried out will be each apparent to those skilled in the art.

The N²-arylsulfonyl-L-argininamide (I) of this invention forms acid addition salts with any of a variety of inorganic and organic acids. Some of te N²-arylsulfonyl-L-argininamides containing a free carboxyl group, wherein $R_3$, $R_6$, $R_7$, $R_8$ or $R_9$ is hydrogen, forms salts with any of a variety of inorganic and organic bases.

The product of the reactions described above can be isolated in the free form or in the form of salts. In addition, the product can be obtained as pharmaceutically acceptable acid addition salts by reacting one of the free bases with an acid, such as hydrochloric, hydrobromic, hydroiodic, nitric, sulfuric, phosphoric, acetic, citric, maleic, succinic, lactic, tartaric, gluconic, benzoic, methanesulfonic, ethanesulfonic, benzenesulfonic, p-toluenesulfonic acid or the like. In a similar manner, the product can be obtained as pharmaceutically acceptable salts by reacting one of the free carboxylic acids with a base, such as sodium hydroxide, potassium hydroxide, ammonium hydroxide, triethylamine, procaine, dibenzylamine, 1-ephenamine, N,N'-dibenzylethylenediamine, N-ethylpiperidine or the like. Likewise, treatment of the salts with a base or acid results in a regeneration of the free amide.

As stated above, the N²-arylsulfonyl-L-argininamides, and the salts thereof of this invention are characterized by their highly specific inhibitory activity against thrombin as well as by their substantial lack of toxicity, and therefore these compounds are useful in the determination of thrombin in blood as diagnostic reagents, and/or for the medical control or prevention of thrombosis. The compounds of this invention are also useful as an inhibitor of platelet aggregation.

The antithrombotic activity of the N²-arylsulfonyl-L-argininamide (I) of this invention was compared with that of a known antithrombotic agent, N²-(p-tolylsulfonyl)-L-arginine methyl ester, by determining the fibrinogen coagulation time. The measurement of the fibrinogen coagulation time was conducted as follows:

An 0.8 ml aliquot of a fibrinogen solution, which had been prepared by dissolving 150 mg of bovine fibrinogen (Cohn fraction I) supplied by Armour Inc. in 40 ml of a borate saline buffer (pH 7.4), was mixed with 0.1 ml of a borate saline buffer, pH 7.4, (control) or a sample solution in the same buffer, and 0.1 ml of a thrombin solution (5 units/ml) supplied by Mochida Pharmaceutical Co., Ltd. was added to the solutions in an ice bath.

Immediately after mixing, the reaction mixture was transferred from the ice bath to a bath maintained at 25° C. Coagulation times were taken as the period between the time of transference to the 25° C. bath and the time of the first appearance of fibrin threads. In the cases where no drug samples were added, the coagulation time was 50–55 seconds. The experimental results are summarized in Table I. The term "concentration required to prolong the coagulation time by a factor of two" is the concentration of an active ingredient required to prolong the normal coagulation time 50–55 seconds to 100–110 seconds.

The concentration required to prolong the coagulation time by a factor of two for the known antithrombotic agent, $N^2$-(p-tolysulfonyl)-L-arginine methyl ester, was 1,100 $\mu M$. The inhibitors are shown in Table I by indicating R and Ar in the formula (I) and the addition moiety. When a solution containing an $N^2$-arylsulfonyl-L-argininamide of this invention was administered intraveneously into animal bodies, the high antithrombotic activity in the circulating blood was maintained for from one to three hours. The halflife for decay of the anti-thrombotic compounds of this invention in circulating blood was shown to be approximately 60 minutes; the physiological conditions of the host animals (rat, rabbit, dog and chimpanzee) were well maintained. The experimental decrease of fibrinogen in animals caused by infusion of thrombin was satisfactorily controlled by simultaneous infusion of the compounds of this invention.

The acute toxicity values ($LD_{50}$) determined by intraperitoneal administration of substances of formula (I) in mice (male, 20 g) range from about 1,000 to 10,000 milligrams per kilogram of body weight.

On the other hand, $LD_{50}$ values for $N^2$-dansyl-N-butyl-L-argininamide and $N^2$-dansyl-N-methyl-N-butyl-L-argininamide are 75 and 70 milligrams per kilogram, respectively. The therapeutic agents of this invention may be administered alone or in combination with pharmaceutically acceptable carriers, the proportion of which is determined by the solubility and chemical nature of the compound, chosen route of administration and standard pharmaceutical practice.

For example, the compounds may be injected parenterally, that is, intramuscularly, intravenously or subcutaneously. For parenteral administration, the compounds may be used in the form of sterile solutions containing other solutes, for example, sufficient saline or glucose to make the solution isotonic. The compounds may be administered orally in the form of tablets, capsules, or granules containing suitable excipients such as starch, lactose, white sugar and the like.

The compounds may be administered sublingually in the form of troches or lozenges in which each active ingredient is mixed with sugar or corn syrups, flavoring agents and dyes, and then dehydrated sufficiently to make the mixture suitable for pressing into solid form. The compounds may be administered orally in the form of solutions which may contain coloring and flavoring agents. Physicians will determine the dosage of the present therapeutic agents which will be most suitable, and dosages vary with the mode of administration and the particular compound chosen. In addition, the dosage will vary with the particular patient under treatment.

When the composition is administered orally, a larger quantity of the active agent will be required to produce the same effect as caused with a smaller quantity given parenterally.

The therapeutic dosage is generally 10–50 mg/kg of active ingredient parenterally, 10–500 mg/kg orally per day. Having generally described the invention, a more complete understanding can be obtained by reference to certain specific examples, which are included for purposes of illustration only and are not intended to be limiting unless otherwise specified.

It is to be understood that the present invenion includes pharmaceutical compositions containing a compound of the invention as an active ingredient. Such compositions may be in the forms described above. In particular, the invention includes such compositions in unit dose form.

PREPARATION A

Arylsulfonyl chlorides

To a well stirred solution of 50.8 g of 2-butoxy-1,3-dimethoxybenzene in 160 ml of carbon tetrachloride was added dropwise 16.1 ml of chlorosulfonic acid at a temperature of 0 to 4° C. The reaction mixture was stirred for one hour at room temperature, poured into crushed ice and then diluted to 300 ml with water.

Upon evaporation of carbon tetrachloride, the resulting aqueous layer was extracted with ether and then neutralized with 2N-NaOH solution to precipitate white crystals which were filtered and dried to give 64.3 g (85.1%) of sodium 3-butoxy-2,4-dimethoxybenzenesulfonate.

To a stirred suspension of 60.0 g of dry, powdery sodium 3-butoxy-2,4-dimethoxybenzenesulfonate in 150 ml of dry dimethylformamide was added dropwise 69 ml of thionyl chloride over a period of 20 minutes at room temperature. The reaction mixture was stirred for 15 minutes and poured gradually into 1,000 ml of ice water and stirred vigorously. After 1 hour, the aqueous layer was decanted and the residual oil was extracted with benzene, washed with water, dried over anhydrous sodium sulfate, distilled to remove the solvent and then distilled in vacuo to give 47.5 g (80.1%) of 3-butoxy-2,4-dimethoxybenzenesulfonyl chloride (Bp 154–5° C/1 mm Hg).

Analysis - Calcd. for $C_{12}H_{15}ClO_5S$ (percent): C, 46.68; H, 5.56 Found (percent): C, 46.71; H, 5.60

The following arysulfonyl chlorides not previously reported in the chemical literature were synthesized by the aforementioned procedure.

| No. | Ar—SO$_2$Cl<br>Ar | Boiling Point<br>(Melting Point) |
|---|---|---|
| 1 |  O(CH$_2$)$_2$CH$_3$ | 165°–166° C./10 mmHg<br>(57.5°–58.5° C.) |
| 2 |  O(CH$_2$)$_3$CH$_3$ | 112°–115° C./1 mmHg<br>(33°–35° C.) |

-continued
| No. | Ar—SO₂Cl Ar | Boiling Point (Melting Point) |
|---|---|---|
| 3 | 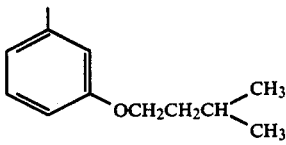 | 127°–129° C./0.5 mmHg |
| 4 | 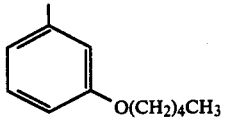 | 148°–150° C./1 mmHg |
| 5 | 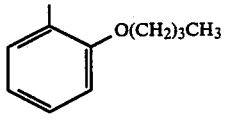 | 143°–145° C./1 mmHg (48°–51° C.) |
| 6 | 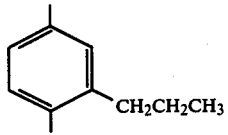 | (41°–2° C.) |
| 7 | 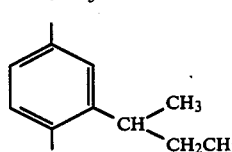 | 139°–140° C./1 mmHg |
| 8 | 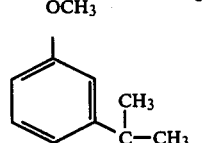 | 129.5°–132° C./1 mmHg |
| 9 | 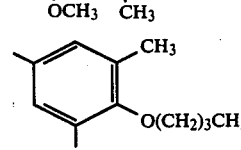 | 145°–148° C./1 mmHg |
| 10 | 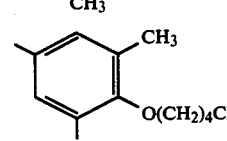 | 151.5°–153.5° C./1.5 mmHg |
| 11 | 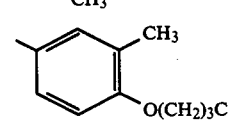 | 155°–156° C./2 mmHg |
| 12 | 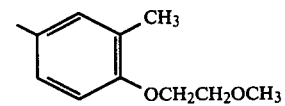 | (44°–45° C.) |
| 13 | 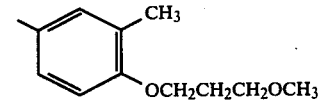 | 187° C./1 mmHg |
| 14 | 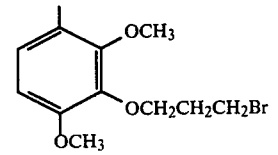 | 198°–200° C./2 mmHg |

-continued
| No. | Ar—SO₂Cl Ar | Boiling Point (Melting Point) |
|---|---|---|
| 15 | 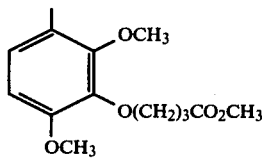 | 210°–220° C./1 mmHg |
| 16 | 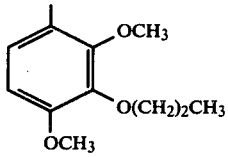 | 160°–162° C./2 mmHg |
| 17 | 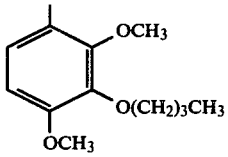 | 154°–155° C./1 mmHg |
| 18 | 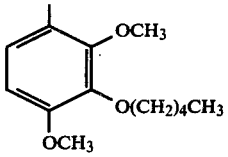 | 170°–172° C./2 mmHg |
| 19 | 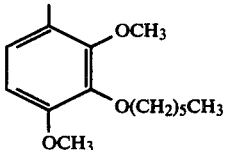 | 183°–185° C./1 mmHg |
| 20 | 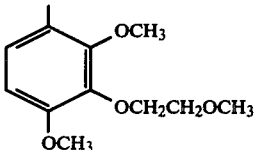 | (46°–47° C.) |
| 21 | 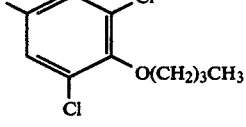 | 131° C./1 mmHg |
| 22 | 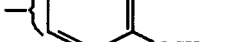 | (65°–66° C.) |
| 23 |  | (30°–32° C.) |
| 24 | 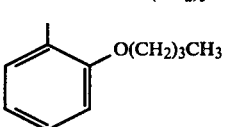 | 208°–210° C./1 mmHg |
| 25 | 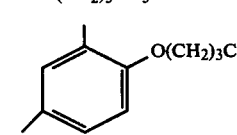 | 178°–179° C./2 mmHg |

| No. | Ar—SO₂Cl Ar | Boiling Point (Melting Point) |
|---|---|---|
| 26 | 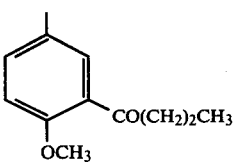 | Oily Substance |
| 27 | 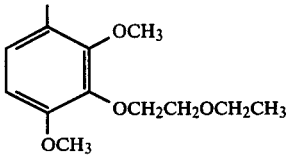 | 165°–168° C./1 mmHg |
| 28 | 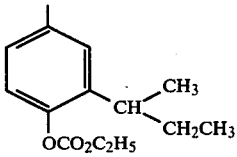 | Oily Substance |
| 29 | 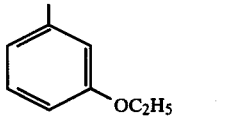 | 109°–110° C./1.5 mmHg |
| 30 | 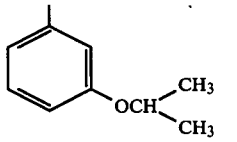 | 111°–116° C./1 mmHg |
| 31 | 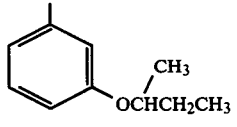 | Oily Substance |
| 32 | 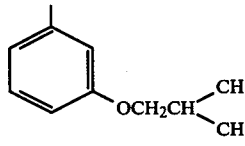 | Oily Substance |
| 33 | 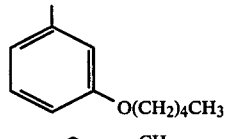 | 148°–150° C./1 mmHg |
| 34 | 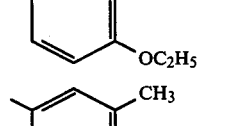 | 152°–153° C./2 mmHg |
| 35 | 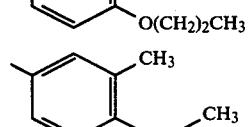 | 133°–134° C./1 mmHg |
| 36 | 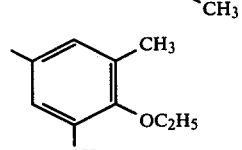 | 142°–143° C./1 mmHg |
| 37 | 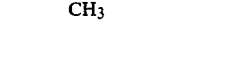 | 121°–122° C./1 mmHg |

-continued
| No. | Ar—SO$_2$Cl Ar | Boiling Point (Melting Point) |
|---|---|---|
| 38 | 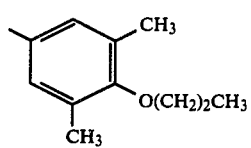 | 133°–135° C./1 mmHg |
| 39 | 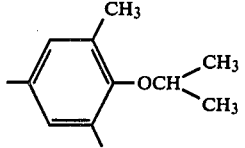 | 136°–139° C./1 mmHg |
| 40 | 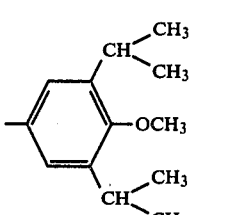 | (95°–6° C.) |
| 41 | 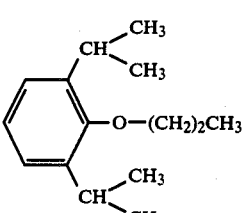 | (101°–103° C.) |
| 42 | 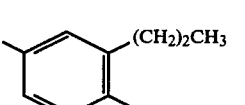 | 142°–144° C./1 mmHg |
| 43 | 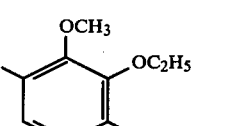 | (50°–51° C.) |
| 44 | 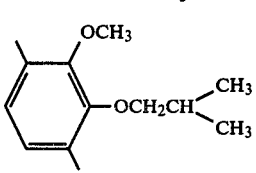 | 158°–160° C./1 mmHg |
| 45 | 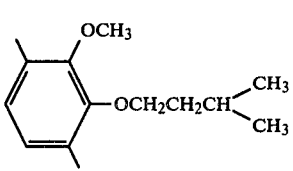 | 159°–160° C./1 mmHg |
| 46 | 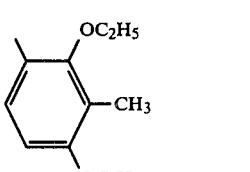 | 151°–2° C./1 mmHg |

| No. | Ar—SO₂Cl Ar | Boiling Point (Melting Point) |
|---|---|---|
| 47 | 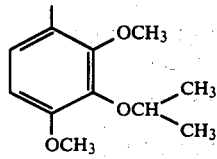 | 158°–159° C./1 mmHg |

EXAMPLE 1

(A) Ethyl 1-[$N^G$-nitro-$N^2$-(tert-butoxycarbonyl)-L-arginyl]-4-methyl-2-piperidinecarboxylate To a stirred solution of 31.9 g of $N^G$-nitro-$N^2$-(tert-butoxycarbonyl)-L-arginine 31.9 g in 400 ml of dry tetrahydrofuran and 14 ml of triethylamine was added 14 ml of isobutyl chloroformate while keeping the temperature below −5° C. After 15 minutes, to this was added 17.1 g of ethyl 4-methyl-2-piperidinecarboxylate, and then the mixture stirred at −5° C. for 15 minutes. At the end of this period, the reaction mixture was warmed to room temperature. The solvent was evaporated and the residue taken in 800 ml of ethyl acetate, and washed successively with 200 ml of water, 100 ml of 5% sodium bicarbonate solution, 100 ml of 10% citric acid solution and 200 ml of water. The ethyl acetate solution was dried over anhydrous sodium sulfate. Upon evaporation of the solvent, the residue was dissolved in 80 ml of chloroform, and the solution was applied to a column of 800 g of silica gel packed in chloroform. The product was eluted first with chloroform, and then 3% methanol-chloroform. The fraction eluted fro 3% methanol-chloroform was evaporated to dryness to give 29.7 g (63%) of ethyl 1-[$N^G$-nitro-$N^2$-(tert-butoxycarbonyl)-L-arginyl]-4-methyl-2-piperidinecarboxylate in the form of a syrup.

I.R. (KBr): 3,320, 1,710, 1,640, 1,240 cm⁻¹

(B) Ethyl 1-$N^G$-nitro-L-arginyl)-4-methyl-2-piperidinecarboxylate hydrochloride:

To a stirred solution of 29.7 g of ethyl 1-[$N^G$-nitro-$N^2$-(tert-butoxycarbonyl)-L-arginyl]-4-methyl-piperidinecarboxylate in 200 ml of ethyl acetate was added 150 ml of 20% dry HCl-ethylacetate while keeping the temperature at 0° C. After 3 hours, a gummy substance which precipitated was separated by decantation and then washed with dry ether to give 20.5 g of ethyl 1-($N^G$-nitro-L-arginyl)-4-2-piperidinecarboxylate hydrochloride in the form of an amorphous solid.

(C) Ethyl 1-[$N^G$-nitro-$N^2$-(3-butoxy-2,4-dimethoxyphenylsulfonyl)-L-arglnyl]-4-methyl-2-piperidinecarboxylate To a solution of 6.0 g of ethyl 1-($N^G$-nitro-L-arginyl)-4-methyl-2-piperidinecarboxylate hydrochloride and 5.4 g of 3-butoxy-2,4-dimethoxybenzenesulfonyl chloride in 20 ml of water and 80 ml of benzene was added 3.7 g of sodium bicarbonate, and stirring was continued for 4 hours at room temperature. At the end of this period, the solvent was evaporated and the residue dissolved in 100 ml of ethyl acetate, and washed successively with 30 ml of 10% citric acid aqueous solution, 30 ml of saturated sodium bicarbonate aqueous solution and 30 ml of saturated sodium chloride aqueous solution.

The ethyl acetate layer was dried over anhydrous sodium sulfate. Upon evaporation of the solvent, the residue was chromatographed on 50 g of silica gel, washed with chloroform and eluted with 3% methanol-chloroform. The fraction eluted from 3% methanol-chloroform was evapaorated to give 6.3 g (66% of ethyl 1-[$N^G$-nitro-$N^2$-(3-butoxy-2,4-dimethyoxyphenylsulfonyl)-L-arginyl]-4-methyl-2-piperidinecarboxylate in the form of an amorphous solid.

I.R. (KBr): 3,400, 1,740, 1630 cm⁻¹

(D) Ethyl 1-[$N^2$-(3-butoxy-2,4-dimethoxyphenylsulfonyl)-L-arginyl]-4-methyl-2-piperidinecarboxylate acetate To a solution of 6.3 g of ethyl 1-[$N^G$-nitro-$N^2$-(3-butoxy-2,4-dimethoxyphenylsulfonyl)-L-arginyl]-4-methyl-2-piperidinecarboxylate in 140 ml of ethanol, 40 ml of acetic acid and 20 ml of water was added 0.8 g of palladium-black and then the mixture was shaken in a hydrogen atmosphere for 24 hours at room temperature. At the end of this period, the catalyst was separated by filtration and the solution was evaporated to give an oily substance. The residue was dissolved in ethanol and reprecipitated with ether to give 5.8 g (90% of ethyl 1-[$N^2$-(3-butoxy-2,4-dimethoxyphenylsulfonyl)-L-arginyl]-4-methyl-2-piperidinecarboxylate acetate.

I.R. (KBr): 3,400, 1,735, 1,625 cm⁻¹

Analysis–Calcd. for $C_{27}H_{45}O_8N_5S \cdot C_2H_4O_2$ (percent): C, 52.79; H, 7.49; N, 10.62 Found (percent): C, 52,83; H, 7.65; N, 10.43.

(E) 1-[$N^2$-(3-butoxy-2,4-dimethoxyphenylsulfonyl)-L-arginyl]-4-methyl-2-piperidinecarboxylic acid To a solution of 5.8 g of ethyl 1-[$N^2$-(3-butoxy-2,4-dimethoxyphenylsulfonyl)-L-arginyl]-4-methyl-2-piperidinecarboxylate acetate in 80 ml of ethanol and 40 ml of water was added 10 ml of 2N NaOH aqueous solution at room temperature and stirring was continued overnight at room temperature. At the end of this period, the reaction solvent was distilled off under reduced pressure at a temperature below 30° C. The residue was dissolved in a small amount of water and then neutralized with 2N NCl to precipitate a white gummy substance. The aqueous solution was separated by decantation and the white precipitate was dissolved in 200 ml of chloroform, washed with 30 ml of water and then dried over anhydrous sodium sulfate. Upon evaporation of solvent, there was obtained 4.0 g (79%) of 1-[$N^2$-(3-butoxy2,4-dimethoxyphenylsulfonyl)-L-arginyl]-4-methyl-2-piperidinecarboxylic acid in the form of an amorphous solid.

I.R. (KBr): 3,350, 1,630, 1,460, 1,090 cm⁻¹

Analysis - Calcd. for $C_{25}H_{41}O_8N_5S$ (percent): C, 52.51; H, 7.24N, 12.25 Found (percent): C, 51.99; H, 7.15; N, 12.30

EXAMPLE 2

(A)

$N^G$-nitro-$N^2$-(3-tert-butyl-4-methoxyphenylsulfonyl)-L-arginyl-N-tetrahydrofurfurylglycine benzyl ester To a stirred solution of 2.5 g of $N^G$-nitro-L-arginyl-N-tetrahydrofurfurylglycine benzyl ester hydrochloride prepared from $N^G$-nitro-$N^2$-(tert-butoxycarbonyl)-L-arginine in accordance with the procedures (A) and (B) of Example 1, and 1.5 g of 3-tert-butyl-4-methoxybenzenesulfonyl chloride in 10 ml of water and 40 ml of dioxane was added 1 g of sodium bicarbonate and then stirring was continued at room temperature for 4 hours. Upon evaporation of the reaction solvent, the residue was dissolved in 50 ml of ethyl acetate and washed consecutively with 20 ml of 1N HCl, 20 ml of saturated NaCl solution, 20 ml of saturated NaHCO$_3$ solution and 20 ml of saturated NaCl solution. The organic layer was dried over anhydrous sodium sulfate and the solvent distilled off. The residue was chromatographed on 50 g of silica gel and the fraction eluted from 3% methanol-chloroform was evaporated to dryness to give 2.7 g (80%) of $N^G$-nitro-$N^2$-(3-tert-butyl-4-methoxyphenylsulfonyl)-L-arginyl-N-tetrahydrofurylglycine benzyl ester in the form of an amorphous solid.

I.R. (KBr): 3,400, 1,740, 1,625, 1,260 cm$^{-1}$ (B)

$N^2$-(3-tert-butyl-4-methoxyphenylsulfonyl)-L-arginyl-N-tetrahydrofurfurylglycine To a solution of 2.7 g of $N^G$-nitro-$N^2$-(3-tert-butyl-4-methoxyphenylsulfonyl)-L-arginyl-N-tetrahydrofurfurylglycine benzyl ester in 30 ml of ethanol, 10 ml of acetic acid and 10 ml of water was added 0.5 g of palladium black and then the mixture was shaken in a hydrogen atmosphere for 24 hours at room temperature. The solution was filtered to remove the catalyst and evaporated to give an oily product.

This was taken up in water and then evaporated to dryness several times by azeotropic distillation. Reprecipitation of the residue with ethanol-methanol gave 1.5 g (69%) of $N^2$-(3-tert-butyl-4-methoxyphenylsulfonyl)-L-arginyl-N-tetrahydrofurfurylglycine.

I.R. (KBr): 3,400, 1,635, 1,260, 1,160 cm$^{-1}$

Analysis - Calcd. for $C_{24}H_{39}O_7N_5S$ (percent): C, 53.21; H, 7.26 N, 12.93 Found (percent): C, 53,16; H, 7.05; N, 12.91

Various other $N^2$-arylsulfonyl-L-argininamides or acid addition, salts thereof were synthesized in accordance with the procedures of the above examples, and the test results are summarized in Table 1.

Table 1

| No. | Compound (I): $H_2N-\underset{HN}{\overset{\|}{C}}-\overset{H}{\overset{\|}{N}}-CH_2CH_2CH_2\underset{H-N-SO_2-Ar}{\overset{\|}{C}}HCOR$ Ar | R | Addition moiety | Concentration required to prolong coagulation time by a factor of two (μM) | Preparation Procedure (Ex. No.) | Elemental Analysis Upper: Calcd. (%) Lower: Found (%) C | H | N | I.R. (KBr) (cm$^{-1}$) |
|---|---|---|---|---|---|---|---|---|---|
| 1 | 3-O(CH$_2$)$_2$CH$_3$-phenyl | 4-methylpiperidine-2-COOH | — | | 1 | 53.10 / 52.93 | 7.09 / 7.20 | 14.08 / 14.00 | 3,300 (broad) 1,630 1,160 |
| 2 | 2-O(CH$_2$)$_3$CH$_3$-phenyl | " | — | | " | 53.98 / 53.77 | 7.29 / 7.18 | 13.69 / 13.60 | 3,300 (broad) 1,620 1,160 |
| 3 | 3-O(CH$_2$)$_3$CH$_3$-phenyl | " | — | 0.8 | " | 53.98 / 53.71 | 7.29 / 7.21 | 13.69 / 13.28 | 3,300 (broad) 1,620 1,155 |
| 4 | " | N-(tetrahydrofurfuryl)-CH$_2$COOH | — | | 2 | 52.35 / 52.27 | 7.07 / 7.19 | 13.27 / 13.00 | 3,370, 1,630 1,255, 1,155 |
| 5 | 3-O(CH$_2$)$_4$CH$_3$-phenyl | 4-methylpiperidine-2-COOH | — | | 1 | 54.83 / 54.95 | 7.48 / 7.46 | 13.32 / 13.41 | 3,350 (broad) 1,620 1,155 |
| 6 | 2-CH$_2$CH$_2$CH$_3$, 4-OCH$_3$-phenyl | N-(tetrahydrofurfuryl)-CH$_2$COOH | — | 1.5 | 2 | 52.35 / 52.41 | 7.07 / 7.15 | 12.27 / 12.46 | 3,380, 1,630 1,255, 1,135 |

Table 1-continued

Compound $$\begin{array}{c}HN\quad H\\ \diagdown\!\!\diagup\\ C-N-CH_2CH_2CH_2CHCOR\\ \diagup\quad\quad\quad |\\ H_2N\quad\quad\quad H-N-SO_2-Ar\end{array}\quad (I)$$

| No. | Ar | R | Addition moiety | Concentration required to prolong coagulation time by a factor of two (μM) | Preparation Procedure (Ex. No.) | Elemental Analysis Upper: Calcd. (%) Lower: Found (%) C / H / N | I.R. (KBr) (cm$^{-1}$) |
|---|---|---|---|---|---|---|---|
| 7 | 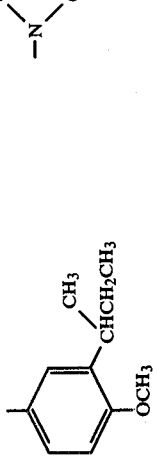 | CH$_2$CH$_2$OCH$_3$ 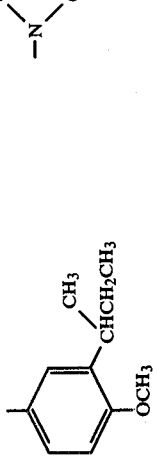 | — | 6.4 | " | 51.24 / 7.23 / 13.58<br>51.34 / 7.46 / 13.29 | 3,350, 1,630<br>1,250, 1,150 |
| 8 | 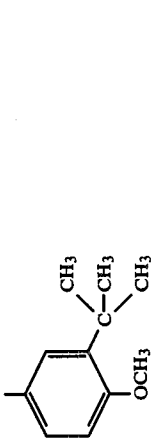 | " | — | 13 | " | 51.24 / 7.23 / 13.58<br>51.38 / 7.15 / 13.62 | 3,350, 1,630<br>1,255, 1,155 |
| 9 | " |  | — | 2 | " | 53.21 / 7.26 / 12.93<br>53.16 / 7.05 / 12.91 | 3,400, 1,630<br>1,260, 1,160 |
| 10 | " |  | — | 0.75 | 1 | 54.83 / 7.48 / 13.32<br>54.97 / 7.48 / 13.36 | 3,400, 1,630<br>1,260, 1,160 |
| 11 |  |  | — | 4 | 2 | 53.21 / 7.26 / 12.93<br>52.95 / 7.31 / 13.15 | 3,375, 1,630<br>1,255, 1,145 |

Table 1-continued

Compound (I):

$$HN=C(NH_2)-NH-CH_2CH_2CH_2CH_2CHCOR$$
$$H-N-SO_2-Ar$$

| No. | Ar | R | Addition moiety | Concentration required to prolong coagulation time by a factor of two (μM) | Preparation Procedure (Ex. No.) | Elemental Analysis Upper: Calcd. (%) Lower: Found (%) | | | I.R. (KBr) (cm$^{-1}$) |
|---|---|---|---|---|---|---|---|---|---|
| | | | | | | C | H | N | |
| 12 | 2-CH$_3$, 4-OCH$_2$CH$_2$OCH$_3$-phenyl | -N(CH$_2$CH$_2$OCH$_3$)(CH$_2$COOH) | — | | " | 48.73 / 48.93 | 6.82 / 6.90 | 13.53 / 13.48 | 3,300, 1,620, 1,110 |
| 13 | " | 4-methyl-2-carboxy-piperidino | — | | 1 | 52.35 / 52.46 | 7.09 / 7.08 | 13.27 / 13.11 | 3,350, 1,610, 1,140 |
| 14 | 2-CH$_3$, 4-O(CH$_2$)$_3$OCH$_3$-phenyl | " | — | | " | 53.21 / 53.11 | 7.26 / 7.56 | 12.93 / 12.78 | 3,365, 1,620, 1,245, 1,150 |
| 15 | 2,6-(CH$_3$)$_2$, 4-O(CH$_2$)$_3$CH$_3$-phenyl | " | — | | " | 55.63 / 55.49 | 7.66 / 7.54 | 12.98 / 13.01 | 3,350, 1,610, 1,400, 1,140 |
| 16 | 2,6-(CH$_3$)$_2$, 4-O(CH$_2$)$_4$CH$_3$-phenyl | " | — | 1 | 1 | 56.39 / 56.43 | 7.83 / 7.85 | 12.65 / 12.49 | 3,350, 1,620, 1,380, 1,150 |
| 17 | " | -N(CH$_2$-tetrahydrofuran-2-yl)(CH$_2$COOH) | — | 3 | 2 | 54.81 / 54.76 | 7.61 / 7.60 | 12.29 / 12.35 | 3,350, 1,630, 1,145 |

Table 1-continued

Compound $$HN\phantom{a}H$$
$$\phantom{HN}\diagdown\phantom{H}|$$
$$\phantom{HN}C-N-CH_2CH_2CH_2CHCOR \quad (I)$$
$$H_2N\diagup \phantom{C-N-CH_2CH_2CH_2C}|$$
$$\phantom{H_2N\diagup C-N-CH_2CH_2CH_2C}H-N-SO_2-Ar$$

| No. | Ar | R | Addition moiety | Concentration required to prolong coagulation time by a factor of two (μM) | Preparation Procedure (Ex. No.) | Elemental Analysis Upper: Calcd. (%) Lower: Found (%) | | | I.R. (KBr) (cm$^{-1}$) |
|---|---|---|---|---|---|---|---|---|---|
| | | | | | | C | H | N | |
| 18 | 4-methyl-2-(CH(CH₃)CH₂CH₃)-phenol | piperidine-2-COOH with 4-CH₃ | — | | 1 | 53.99 54.15 | 7.29 7.28 | 13.69 13.58 | 3,400, 1,630 1,150 |
| 19 | 4-methyl-2-C(CH₃)₃-anisole | piperidine-2-COOC₂H₅ with 4-CH₃ | CH₃COOH | | " | 54.79 54.86 | 7.72 7.54 | 11.41 11.46 | 3,400, 1,740 1,630 |
| 20 | 4-methyl-2-CO(CH₂)₂CH₃-anisole | piperidine-2-COOH with 4-CH₃ | — | | " | 54.23 54.48 | 7.10 7.04 | 12.65 12.63 | 3,400, 1,680 1,630, 1,150 |
| 21 | 2-Cl-4-C(CH₂)₃CH₃-phenyl | " | — | | 1 | 47.58 47.36 | 6.08 6.15 | 12.06 12.08 | 3,350, 1,630 1,150 |
| 22 | 4-methyl-2-OCH₃-1-O(CH₂)₂CH₃-phenyl | " | — | | " | 52.35 52.19 | 7.07 7.02 | 13.27 13.41 | 3,420, 1,630 1,270, 1,165 |
| 23 | 4-methyl-2-O(CH₂)₃CH₃-1-O(CH₂)₃CH₃-phenyl | " | — | | " | 55.55 55.73 | 7.77 7.68 | 12.00 11.99 | 3,410, 1,630 1,290, 1,170 |

Table 1-continued

Compound (I):

$$HN\!\!=\!\!\underset{H_2N}{\overset{H}{C}}\!\!-\!\!\underset{}{\overset{H}{N}}\!\!-\!\!CH_2CH_2CH_2\underset{H\!-\!N\!-\!SO_2\!-\!Ar}{CHCOR}$$

| No. | Ar | R | Addition moiety | Concentration required to prolong coagulation time by a factor of two (μM) | Preparation Procedure (Ex. No.) | Elemental Analysis Upper: Calcd. Lower: Found (%) | | | I.R. (KBr) (cm⁻¹) |
|---|---|---|---|---|---|---|---|---|---|
| | | | | | | C | H | N | |
| 24 | 4-methyl-2,5-bis(O-(CH₂)₃CH₃)phenyl | " | — | | " | 55.55<br>55.64 | 7.77<br>7.96 | 12.00<br>11.82 | 3,420, 1,650<br>1,260, 1,165 |
| 25 | 4-methyl-3-(O-(CH₂)₃CH₃), CH₃(CH₂)₃O-phenyl | tetrahydrofurfuryl-CH₂-N(CH₂COOH)- | — | | 2 | 54.07<br>54.05 | 7.56<br>7.81 | 11.68<br>11.43 | 3,350, 1,630<br>1,160 |
| 26 | 2,3-dimethoxy-4-(O-(CH₂)₂CH₃), OCH₃-phenyl | 4-methyl-2-COOH piperidine-N-CH₂COOH | — | | 1 | 51.68<br>51.44 | 7.06<br>7.12 | 12.56<br>12.67 | 3,350, 1,630<br>1,380, 1,090 |
| 27 | " | " | — | 0.9 | " | 52.51<br>51.99 | 7.24<br>7.15 | 12.25<br>12.30 | 3,350, 1,630<br>1,460, 1,090 |
| 28 | " | CH₂CH₂OCH₃-N(CH₂COOH)- | — | | 2 | 49.17<br>49.31 | 7.01<br>7.13 | 12.47<br>12.52 | 3,300, 1,630<br>1,400, 1,090 |
| 29 | " | (CH₂)₄CH₃-N(CH₂COOH)- | — | | " | 52.33<br>52.47 | 7.55<br>7.23 | 12.21<br>12.31 | 3,350, 1,630<br>1,460 |

Table 1-continued
Compound
$$\begin{array}{c} HN \quad H \\ \diagdown \\ C-N-CH_2CH_2CH_2CHCOR \\ \diagup \qquad\qquad | \\ H_2N \qquad H-N-SO_2-Ar \end{array} \quad (I)$$
| No. | Ar | R | Addition moiety | Concentration required to prolong coagulation time by a factor of two (μM) | Preparation Procedure (Ex. No.) | Elemental Analysis Upper: Calcd. (%) Lower: Found C | | H | N | I.R. (KBr) (cm$^{-1}$) |
|---|---|---|---|---|---|---|---|---|---|---|
| 30 | " |  | — | | " | 52.33 52.51 | | 7.55 7.61 | 12.21 12.18 | 3,400, 1,620 1,095 |
| 31 |  | 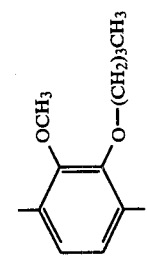 | — | | 2 | 54.07 54.12 | | 7.56 7.34 | 11.58 11.52 | 3,350, 1,620 1,090 |
| 32 | " | 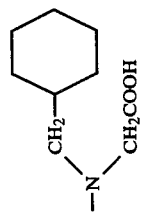 | — | | " | 53.31 53.28 | | 7.40 7.28 | 11.96 11.77 | 3,350, 1,620 1,450 |
| 33 | " | 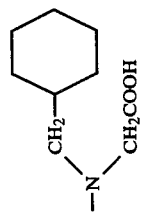 | — | | " | 53.87 53.72 | | 6.43 6.54 | 12.08 12.00 | 3,400, 1,630 1,090 |
| 34 | " | 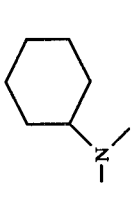 | — | | " | 55.33 55.49 | | 6.80 6.71 | 11.53 11.51 | 3,370, 1,635 1,580, 1,090 |

Table 1-continued

Compound (I):

$$\underset{H_2N}{\overset{HN}{>}}C-\overset{H}{\underset{|}{N}}-CH_2CH_2\overset{H-N-SO_2-Ar}{\underset{|}{CH}}CHCOR$$

| No. | Ar | R | Addition moiety | Concentration required to prolong coagulation time by a factor of two (μM) | Preparation Procedure (Ex. No.) | Elemental Analysis Upper: Calcd. (%) Lower: Found (%) | | | I.R. (KBr) (cm$^{-1}$) |
|---|---|---|---|---|---|---|---|---|---|
| | | | | | | C | H | N | |
| 35 | " | –N(CH₂C₆H₅)CH₂COOH | — | | " | 55.33 55.21 | 6.80 6.75 | 11.53 11.34 | 3,350, 1,620 1,455, 1,090 |
| 36 | 2,3-dimethoxy-6-methyl, O–(CH₂)₄CH₃ | 4-methyl-2-COOH piperidine | — | 0.8 | 1 | 53.30 53.41 | 7.41 7.42 | 11.96 12.03 | 3,350, 1,620 1,455, 1,090 |
| 37 | 2,3-dimethoxy-6-methyl, O–(CH₂)₅CH₃ | " | — | | " | 54.06 54.16 | 7.58 7.69 | 1.68 11.70 | 3,350, 1,625 1,460, 1,090 |
| 38 | 2,3-dimethoxy-6-methyl, OCH₂CH₂OCH₃ | " | — | 5 | " | 50.25 50.39 | 6.85 6.79 | 12.21 12.30 | 3,400, 1,630 1,455, 1,090 |
| 39 | 2,3-dimethoxy-6-methyl, OCH₂CH₂CH₂Br | " | — | | " | 45.28 45.46 | 6.02 5.95 | 11.00 11.26 | 3,400, 1,620 1,080 |

Table 1-continued

| No. | Ar | R | Addition moiety | Concentration required to prolong coagulation time by a factor of two (μM) | Preparation Procedure (Ex. No.) | Elemental Analysis Upper: Calcd. Lower: Found (%) C | H | N | I.R. (KBr) (cm$^{-1}$) |
|---|---|---|---|---|---|---|---|---|---|
| 40 | (OCH$_3$, OCH$_2$OCH$_2$CH$_3$, OCH$_3$ substituted phenyl) | " | — | 4 | " | 51.09 51.20 | 7.03 7.14 | 11.92 11.87 | 3,375, 1,620 1,455, 1,090 |
| 41 | (OCH$_3$, O—(CH$_2$)$_3$CO$_2$CH$_3$, OCH$_3$ substituted phenyl) | N(CH$_2$CH$_2$OCH$_3$)(CH$_2$COOH) | — | | 2 | 46.69 46.48 | 6.30 6.41 | 11.84 11.88 | 3,400, 1,720 1,630, 1,080 |
| 42 | (OCH$_3$, O—(CH$_2$)$_3$CH$_3$, OCH$_3$ substituted phenyl) | 4-CH$_3$-piperidine-2-COOCH$_2$CH$_3$ | CH$_3$COOH | | 1 | 52.79 52.83 | 7.49 7.65 | 10.62 10.43 | 3,400, 1,735 1,625 |
| 43 | (OCH$_3$, OCH$_2$CH$_2$CH(CH$_3$)$_2$ substituted phenyl) | 4-CH$_3$-piperidine-2-COOH | — | | 1 | 54.83 54.15 | 7.48 7.03 | 13.32 13.85 | 3,300, 1,625 1,160 |
| 44 | (OCH(CH$_3$)CH$_2$CH$_3$ substituted phenyl) | " | | 0.2 | 2 | 53.98 53.77 | 7.29 7.09 | 13.69 13.38 | 3,340, 1,620 1,380, 1,155 |

Table 1-continued $$\begin{array}{c} \text{HN} \quad \text{H} \\ \| \quad | \\ \text{H}_2\text{N}-\text{C}-\text{N}-\text{CH}_2\text{CH}_2\text{CH}_2\text{CHCOR} \\ | \\ \text{H}-\text{N}-\text{SO}_2-\text{Ar} \end{array} \quad (I)$$

| No. | Ar | R | Addition moiety | Concentration required to prolong coagulation time by a factor of two (μM) | Preparation Procedure (Ex. No.) | Elemental Analysis Upper: Calcd. Lower: Found (%) C | H | N | I.R. (KBr) (cm$^{-1}$) |
|---|---|---|---|---|---|---|---|---|---|
| 45 | 3-(OCH₂CH(CH₃)CH₃)-C₆H₄ | " | | 0.1 | 2 | 53.98 / 53.79 | 7.29 / 7.11 | 13.69 / 13.81 | 3,340, 1,610 1,380, 1,155 |
| 46 | 3-(OCH(CH₃)CH₃)-C₆H₄ | " | | 0.65 | 2 | 53.10 / 53.00 | 7.09 / 7.00 | 14.08 / 14.00 | 3,350, 1,620 1,380, 1,155 |
| 47 | 4-(O(CH₂)₃CH₃)-C₆H₄ | " | | | 2 | 53.98 / 53.71 | 7.29 / 7.08 | 13.69 / 13.72 | 3,350, 1,620 1,380, 1,155 |
| 48 | 2-CH₃, 4-(OCH(CH₃)CH₃)-C₆H₃ | " | | 0.6 | 2 | 53.98 / 53.92 | 7.29 / 7.33 | 13.69 / 13.60 | 3,300, 1,600 1,380, 1,130 |
| 49 | 2-(CH₂)₂CH₃, 4-(O(CH₂)₂CH₃)-C₆H₃ | " | | | 2 | 55.63 / 55.59 | 7.66 / 7.74 | 12.98 / 12.99 | 3,320, 1,620 1,380, 1,130 |
| 50 | 2-CH₃, 4-(O(CH₂)₂CH₃)-C₆H₃ | " | | 0.2 | 2 | 54.83 / 54.80 | 7.48 / 7.53 | 13.32 / 13.30 | 3,300, 1,630 1,380, 1,150 |

Table 1-continued $$\begin{array}{c}HN\phantom{xx}H\\\phantom{xxx}\diagdown\phantom{x}|\\\phantom{xxx}C-N-CH_2CH_2CH_2CHCOR\\\phantom{xx}\diagup\phantom{xxxxxxxxxxx}|\\H_2N\phantom{xxxxxxxxx}H-N-SO_2-Ar\end{array}\quad (I)$$

| No. | Ar | R | Addition moiety | Concentration required to prolong coagulation time by a factor of two (μM) | Preparation Procedure (Ex. No.) | Elemental Analysis Upper: Calcd. (%) Lower: Found (%) | | | I.R. (KBr) (cm$^{-1}$) |
|---|---|---|---|---|---|---|---|---|---|
| | | | | | | C | H | N | |
| 51 |  | " | | | 2 | 56.39 56.51 | 7.83 7.78 | 12.65 12.56 | 3,350, 1,620 1,460, 1,155 |
| 52 |  | " | | | 2 | 57.80 57.85 | 8.14 8.69 | 12.04 11.98 | 3,350, 1,620 1,380, 1,140 |
| 53 |  | " | | 0.1 | 2 | 54.83 54.81 | 7.48 7.52 | 13.32 13.27 | 3,350, 1,615 1,380, 1,150 |
| 54 |  | " | | | 2 | 53.21 53.39 | 7.26 7.30 | 12.93 12.88 | 3,350, 1,620 1,360, 1,155 |
| 55 |  | " | | | 2 | 53.02 53.15 | 7.60 7.57 | 12.88 12.86 | 3,350, 1,620 1,380, 1,160 |

Table 1-continued
Compound
$$\begin{array}{c} HN \quad H \\ \diagdown \quad | \\ C-N-CH_2CH_2CH_2CHCOR \\ \diagup \quad \quad \quad | \\ H_2N \quad \quad H-N-SO_2-Ar \end{array} \quad (I)$$
| No. | Ar | R | Addition moiety | Concentration required to prolong coagulation time by a factor of two (μM) | Preparation Procedure (Ex. No.) | Elemental Analysis Upper: Calcd. (%) Lower: Found (%) | | | I.R. (KBr) (cm$^{-1}$) |
|---|---|---|---|---|---|---|---|---|---|
| | | | | | | C | H | N | |
| 56 |  | " | | 0.75 | 2 | 52.51 52.43 | 7.24 7.31 | 12.25 12.26 | 3,330, 1,620 1,380, 1,160 |
| 57 | 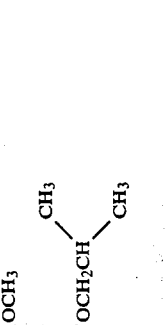 | " | | 0.55 | 2 | 53.30 53.36 | 7.41 7.35 | 11.96 12.01 | 3,330, 1,620 1,380, 1,160 |
| 58 | 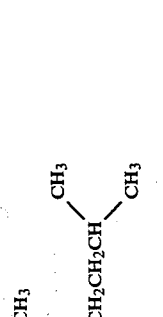 | |  | | 1 | 53.98 54.15 | 7.29 7.26 | 13.69 13.76 | 3,400, 1,620 1,150 |
| 59 | 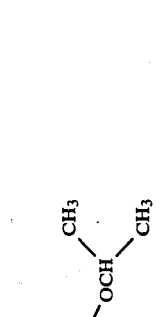 | |  | 0.25 | 1 | 52.51 52.41 | 7.24 7.04 | 12.25 12.05 | 3,350, 1,620 1,380, 1,160 |
| 60 | 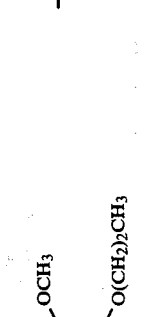 | " | | 0.25 | 1 | 53.98 53.66 | 7.29 7.11 | 13.69 13.23 | 3,300, 1,620 1,380, 1,155 |

Table 1-continued

Compound (I):

$$HN=C(H_2N)-N(H)-CH_2CH_2CHCOR$$
$$\quad\quad\quad\quad\quad\quad\quad H-N-SO_2-Ar$$

| No. | Ar | R | Addition moiety | Concentration required to prolong coagulation time by a factor of two (μM) | Preparation Procedure (Ex. No.) | Elemental Analysis Upper: Calcd. (%) Lower: Found (%) C | H | N | I.R. (KBr) (cm$^{-1}$) |
|---|---|---|---|---|---|---|---|---|---|
| 61 | 2,6-dimethoxy-3-methyl-phenyl (OCH₃, O(CH₂)₃CH₃, OCH₃) | " | | | 1 | 53.30 / 53.21 | 7.41 / 7.18 | 11.96 / 11.89 | 3,350, 1,620 1,380, 1,155 |
| 62 | 2,6-dimethoxy-3-methyl-phenyl (OCH₃, O(CH₂)₂CH(CH₃)₂ OCH₃) | " | | | 1 | 54.06 / 53.90 | 7.58 / 7.48 | 11.68 / 11.48 | 3,350, 1,620 1,380, 1,155 |
| 63 | 2,6-dimethoxy-3-methyl-phenyl | pyridin-2-ylmethyl-N-CH₂COOH | | 2 | 1 | 52.51 / 52.46 | 6.44 / 7.08 | 14.13 / 14.25 | 3,370, 1,620 1,410, 1,090 |
| 64 | 3-isopropoxy-phenyl (OCH(CH₃)₂) | pyridin-3-ylmethyl-N-CH₂COOH | | | 1 | 53.06 / 52.95 | 6.20 / 6.21 | 16.14 / 16.15 | 3,350, 1,620 1,410, 1,150 |
| 65 | " | piperidine-2-carboxylic acid, 4-isopropyl (CH₃, CH₃, CH, COOH) | | | 1 | 54.83 / 54.71 | 7.48 / 7.23 | 13.32 / 13.11 | 3,355, 1,620 1,380, 1,150 |

Table 1-continued

Compound $$\underset{H_2N}{\overset{HN}{>}}C-\overset{H}{\underset{|}{N}}-CH_2CH_2CH_2\overset{R}{\underset{|}{CHCOR}} \quad (I)$$
$$H-\underset{|}{N}-SO_2-Ar$$

| No. | Ar | R | Addition moiety | Preparation Procedure (Ex. No.) | Elemental Analysis Upper: Calcd. (%) Lower: Found (%) | | | Concentration required to prolong coagulation time by a factor of two (μM) | I.R. (KBr) (cm⁻¹) |
| | | | | | C | H | N | | |
|---|---|---|---|---|---|---|---|---|---|
| 66 |  |  | | 1 | 55.63<br>55.56 | 6.66<br>7.58 | 12.98<br>12.79 | | 3,360, 1,620<br>1,380, 1,150 |
| 67 | 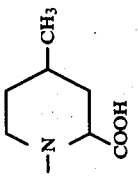 | 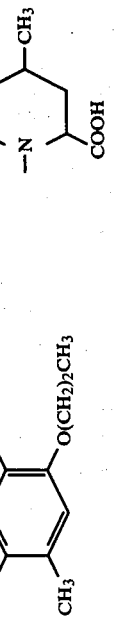 | | 1 | 54.83<br>54.90 | 7.48<br>7.41 | 13.32<br>13.29 | | 3,340, 1,620<br>1,380, 1,150 |
| 68 |  | " | | 1 | 54.83<br>54.77 | 7.48<br>7.50 | 13.32<br>13.35 | | 3,350, 1,620<br>1,385, 1,140 |

The following compounds can be prepared in accordance with the procedures of the above Examples:

1-[N²-(2,4-dimethoxy-3-butoxyphenylsulfonyl)-L-arginyl]-4-ethyl-2-piperidinecarboxylic acid
1-[N²-(2,4-dimethoxy-3-butoxyphenylsulfonyl)-L-arginyl]-4-propyl-2-piperidinecarboxylic acid
2-[N²-(2,4-dimethoxy-3-propoxyphenylsulfonyl)-L-arginyl]-1,2,3,4-tetrahydroisoquinoline-3-carboxylic acid
2-[N²-(2,4-dimethoxy-3-isobutoxyphenylsulfonyl)-L-arginyl]isoindoline-1-carboxylic acid
1-[N²-(2,4-dimethoxy-3-butoxyphenylsulfonyl)-L-arginyl]-2-hexamethyleneiminecarboxylic acid
2-[N²-(3-butoxyphenylsulfonyl)-L-arginyl]isoindoline-1-carboxylic acid
1-[N²-(3-butoxyphenylsulfonyl)-L-arginyl]-4-isopropyl-2-piperidinecarboxylic acid
1-[N²-(3-isopentyloxyphenylsulfonyl)-L-arginyl]-4-methyl-2-piperidinecarboxylic acid
1-[N²-(3-(2-methoxyethoxy)phenylsulfonyl)-L-arginyl]-4-ethyl-2-piperidinecarboxylic acid
N²-(3-butoxyphenylsulfonyl)-L-arginyl-N-butylglycine
N²-(3-butoxyphenylsulfonyl)-L-arginyl-N-(2-methoxyethyl)glycine
N²-(3-butoxyphenylsulfonyl)-L-arginyl-N-(2-methoxyethyl)-α-alanine
1-[N²-(3,5-dimethyl-4-butoxyphenylsulfonyl)-L-arginyl]-4-ethyl-2-piperidinecarboxylic acid
1-[N²-(3,5-dimethyl-4-isobutoxyphenylsulfonyl)-L-arginyl]-4-methyl-2-piperidinecarboxylic acid
N²-(3,5-dimethyl-4-butoxyphenylsulfonyl)-L-arginyl-N-(2-methoxyethyl)glycine
1-[N²-(3tert-butyl-4-methoxyphenylsulfonyl)-L-arginyl]-4-ethyl-2-piperidinecarboxylic acid
1-[N²-(3-isobutyl-4-methoxyphenylsulfonyl)-L-arginyl]-4-isopropyl-2-piperidinecarboxylic acid
1-[N²-(3-butylphenylsulfonyl)-L-arginyl]-4-methyl-2-piperidinecarboxylic acid
1-[N²-(3-isopentylphenylsulfonyl)-L-arginyl]-4-ethyl-2-piperidinecarboxylic acid
N²-(3-butoxyphenylsulfonyl)-L-arginyl-N-benzylglycine
2-[N²-(3-tert-butyl-4-methoxyphenylsulfonyl)-L-arginyl]isoindoline-1-carboxylic acid
1-[N²-(3-tert-butyl-4-methoxyphenylsulfonyl)-L-arginyl]-2-hexamethyleneiminecarboxylic acid
N²-(3-isobutyl-4-methoxyphenylsulfonyl)-L-arginyl-N-cyclohexylglycine
2-[N²-(3-valeryl-4-methoxyphenylsulfonyl)-L-arginyl]isoindoline-1-carboxylic acid
N²-(3-butoxyphenylsulfonyl)-L-arginyl-N-butyl-β-alanine
N²-(3-butoxyphenylsulfonyl)-L-arginyl-N-benzyl-γ-alanine
N²-(3-butoxyphenylsulfonyl)-L-arginyl-N-cyclohexylglycine
N²-(3-butoxyphenylsulfonyl)-L-arginyl-N-benzylglycine

EXAMPLE 3

Tablets suitable for oral administration

Tablets containing the ingredients indicated below may be prepared by conventional techniques.

| Ingredient | Amount per tablet (mg) |
|---|---|
| 1-[N²-(2,4-dimethoxy-3-butoxyphenylsulfonyl)-L-arginyl]-4-methyl-2-piperidinecarboxylic acid | 250 |
| Lactose | 140 |
| Corn starch | 35 |
| Talcum | 20 |
| Magnesium stearate | 5 |
| Total | 450 mg |

EXAMPLE 4

Capsules for oral administration

Capsules of the below were made up by thoroughly mixing together batches of the ingredients and filling hard gelatin capsules with the mixture.

| Ingredient | Amount per capsule (mg) |
|---|---|
| 1-[N²-(2,4-dimethoxy-3-butoxyphenylsulfonyl)-L-arginyl]-4-methyl-2-piperidinecarboxylic acid | 250 |
| Lactose | 250 |
| Total | 500 mg |

EXAMPLE 5

Sterile solution for infusion

The following ingredients are dissolved in water for intravenous perfusion and the resulting solution is then sterilized.

| Ingredients | Amount (g) |
|---|---|
| 1-[N²-(2,4-dimethoxy-3-butoxyphenylsulfonyl)-L-arginyl]-4-methyl-2-piperidinecarboxylic acid | 25 |
| Buffer system | As desired |
| Glucose | 25 |
| Distilled water | 500 |

Having now fully described the invention, it will be apparent to one of ordinary skill in the art that many changes and modifications can be made thereto without departing from the spirit of the invention as set forth herein.

What is claimed as new and desired to be covered by letters patent of the United States is:

1. An N²-arylsulfonyl-L-argininamide of the formula (I):

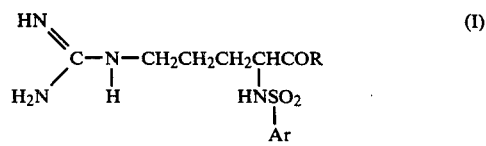

wherein R is selected from group consisting of

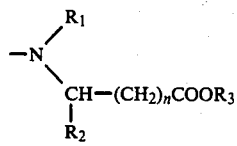

wherein $R_1$ is selected from the group consisting of hydrogen, $C_1$-$C_{10}$ alkyl, $C_3$-$C_{10}$ alkenyl, $C_3$-$C_{10}$ alkynyl, $C_2$-$C_{10}$ alkoxyalkyl, $C_2$-$C_{10}$ alkylthioalkyl, $C_2$-$C_{10}$ alkylsulfinylalkyl, $C_1$-$C_{10}$ hydroxyalkyl, $C_2$-$C_{10}$ carboxyalkyl, $C_3$-$C_{10}$ alkoxycarbonylalkyl, $C_3$-$C_{10}$ alkylcarbonylalkyl, $C_1$-$C_{10}$ haloalkyl, $C_7$-$C_{15}$ aralkyl, $C_8$-$C_{15}$ α-carboxyaralkyl, $C_3$-$C_{10}$ cycloalkyl, $C_4$-$C_{10}$ cycloalkylalkyl, furfuryl, tetrahydrofurfuryl optionally substituted with at least one $C_1$-$C_5$ alkyl, $C_1$-$C_5$ alkoxy or mixtures thereof, 3-furylmethyl, tetrahydro-3-furylmethyl optionally substituted with at least one $C_1$-$C_5$ alkyl, $C_1$-$C_5$ alkoxy or mixtures thereof, tetrahydro-2-pyranylmethyl optionally substituted with at least one $C_1$-$C_5$ alkyl, $C_1$-$C_5$ alkoxy or mixtures thereof, 1,4-dioxa-2-cyclohexylmethyl optionally substituted with at least one $C_1$-$C_5$ alkyl, $C_1$-$C_5$ alkoxy or mixtures thereof, 2-thenyl, 3-thenyl, tetrahydro-2-thenyl optionally substituted with at least one $C_1$-$C_5$ alkyl, $C_1$-$C_5$ alkoxy or mixtures thereof, and tetrahydro-3-thenyl; $R_2$ is selected from the group consisting of hydrogen, $C_1$-$C_{10}$ alkyl, carboxy, $C_2$-$C_{10}$ alkoxycarbonyl, phenyl optionally substituted with at least one $C_1$-$C_5$ alkyl, $C_1$-$C_5$ alkoxy or mixtures thereof, $C_7$-$C_{12}$ aralkyl and ring substituted benzyl wherein said substitutent is $C_1$-$C_5$ alkyl or $C_1$-$C_5$ alkoxy; $R_3$ is selected from the group consisting of hydrogen, $C_1$-$C_{10}$ alkyl, $C_6$-$C_{10}$ aryl, $C_7$-$C_{12}$ aralkyl and 5-indanyl; and n is an integer of 0, 1 or 2

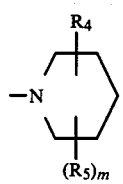

wherein $R_4$ is —$COOR_6$ wherein $R_6$ is selected from the group consisting of hydrogen, $C_1$-$C_{10}$ alkyl, $C_6$-$C_{10}$ aryl, $C_7$-$C_{12}$ aralkyl and 5-indanyl; each $R_5$ independently is hydrogen, $C_1$-$C_{10}$ alkyl; phenyl, $C_1$-$C_5$ alkoxy or carboxy; m is an integer of 1 to 5; $R_4$ is substituted at the 2 or 3-position; and $R_5$ can be substituted at the 2, 3, 4, 5 or 6-position,

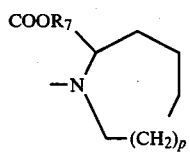

optionally substituted with at least one $C_1$-$C_5$ alkyl, $C_1$-$C_5$ alkoxy or mixtures thereof, wherein $R_7$ is selected from the group consisting of hydrogen, $C_1$-$C_{10}$ alkyl, $C_6$-$C_{10}$ aryl, $C_7$-$C_{12}$ aralkyl and 5-indanyl; and p is an integer of 1, 2, 3, or 4,

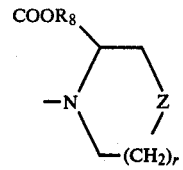

wherein $R_8$ is selected from the group consisting of hydrogen, $C_1$-$C_{10}$ alkyl, $C_6$-$C_{10}$ aryl, $C_7$-$C_{12}$ aralkyl and 5-indanyl; Z is selected from the group consisting of oxy, thio and sulfinyl; and r is an integer of 0 or 1, and

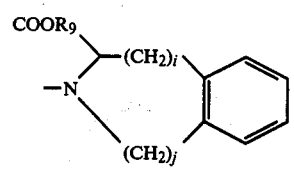

wherein $R_9$ is selected from the group consisting of hydrogen, $C_1$-$C_{10}$ alkyl, $C_6$-$C_{10}$ aryl, $C_7$-$C_{12}$ aralkyl and 5-indanyl; i is an integer of 0, 1 or 2; j is an integer of 0, 1 or 2; and the sum of i + j is an integer of 1 or 2; and Ar is a phenyl group substituted with at least one substituent selected from the group consisting of alkyl, alkoxy and alkylcarbonyl, said substituent being optionally substituted with halo, alkoxy or alkoxycarbonyl, the number of the carbon atoms of each substituent which is attached to the phenyl group being 3 to 7 and the said phenyl group being optionally substituted further with at least one substituent selected from the group consisting of methyl, ethyl, methoxy, ethoxy, hydroxyl and halo.

2. The compound of claim 1, wherein R is selected from the group consisting of

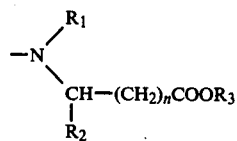

wherein $R_1$ is selected from the group consisting of $C_1$-$C_{10}$ alkyl, $C_2$-$C_{10}$ alkoxyalkyl, $C_7$-$C_{15}$ aralkyl, $C_3$-$C_{10}$ cycloalkyl, $C_4$-$C_{10}$ cycloalkylalkyl, tetrahydrofurfuryl optionally substituted with at least one $C_1$-$C_5$ alkyl, $C_1$-$C_5$ alkoxy or mixtures thereof; $R_2$ is selected from the group consisting of hydrogen, and $C_1$-$C_{10}$ alkyl; $R_3$ is selected from the group consisting of hydrogen, $C_1$-$C_{10}$ alkyl, $C_6$-$C_{10}$ aryl, $C_7$-$C_{12}$ aralkyl and 5-indanyl; and n is an integer of 0, 1 or 2

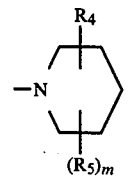

wherein $R_4$ is —$COOR_6$ wherein $R_6$ is selected from the group consisting of hydrogen, $C_1$-$C_{10}$ alkyl, $C_6$-$C_{10}$ aryl, $C_7$-$C_{12}$ aralkyl and 5-indanyl; each $R_5$ independently is hydrogen or $C_1$-$C_{10}$ alkyl; m is an integer of 1 or 2; $R_4$ is substituted at the 2-position; and $R_5$ can be substituted at the 2, 3, 4, 5 or 6-position,

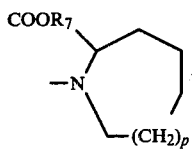

optionally substituted with at least one $C_1-C_5$ alkyl, $C_1-C_5$ alkoxy or mixtures thereof, wherein $R_7$ is selected from the group consisting of hydrogen, $C_1-C_{10}$ alkyl, $C_6-C_{10}$ aryl, $C_7-C_{12}$ aralkyl and 5-indanyl; and p is an integer of 1, 2, 3 or 4,

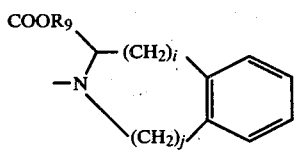

wherein $R_9$ is selected from the group consisting of hydrogen, $C_1-C_{10}$ alkyl, $C_6-C_{10}$ aryl, $C_7-C_{12}$ aralkyl and 5-indanyl; i is an integer of 0, 1 or 2; j is an integer of 0, 1 or 2; and the sum of i + j is an integer of 1 or 2; and Ar is a phenyl group substituted with at least one substituent selected from the group consisting of alkyl, alkoxy and alkylcarbonyl, said substituent being optionally substitued with halo, alkoxy or alkoxycarbonyl, the number of the carbon atoms of each susbstituent which is attached to the phenyl group being 3 to 5 and the said phenyl group being optionally substituted further with at least one substituent selected from the group consisting of methyl, ethyl, methoxy, ethoxy, hydroxyl and halo.

3. The compound of claim 2, which is 1-[$N^2$-(3-butoxyphenylsulfonyl)-L-arginyl]-4-methyl-2-piperidinecarboxylic acid.

4. The compound of claim 2, which is $N^2$-(3-butoxyphenylsulfonyl)-L-arginyl-N-tetrahydrofurfurylglycine 5. The compound of claim 2, which is 1-[$N^2$-(3-isobutoxyphenylsulfonyl)-L-arginyl]-4-ethyl-2-piperidinecarboxylic acid.

6. The compound of claim 2, which is 1-[$N^2$-(3-tert-butyl-4-methoxyphenylsulfonyl)-L-arginyl]-4-methyl-2-piperidinecarboxylic acid.

7. The compound of claim 2, which is 1-[$N^2$-(2,4-dimethoxy-3-butoxyphenylsulfonyl)-L-arginyl]-4-methyl-2-piperidinecarboxylic acid.

8. The compound of claim 2, which is 1-[$N^2$-(2,4-dimethoxy-3-propoxyphenylsulfonyl)-L-arginyl]-4-methyl-2-piperidinecarboxylic acid.

9. The compound of claim 2, which is ethyl 1-[$N^2$-(2,4-dimethoxy-2-butoxyphenylsulfonyl)-L-arginyl]-4-methyl-2-piperidinecarboxylate.

10. The compound of claim 2, which is $N^2$-(2,4-dimethoxy-3-butoxyphenylsulfonyl)-L-arginyl-N-(2-methoxyethyl)glycine.

11. The compound of claim 2, which is 1-[$N^2$-(3-valeryl-4-methoxyphenylsulfonyl)-L-arginyl]-4-methyl-2-piperidinecarboxylic acid.

12. The compound of claim 2, whch is 1-[$N^2$-(3,5-dimethyl-4-butoxyphenylsulfonyl)-L-arginyl]-4-methyl-2-piperidinecarboxylic acid.

13. An anticoagulant containing an $N^2$-arylsulfonyl-L-argininamide of the formula (I):

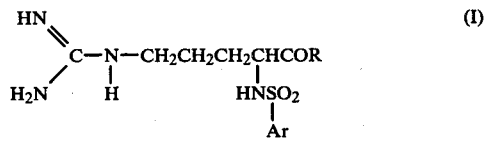

wherein R and Ar are as defined in claim 1, or the pharmaceutically acceptable salt thereof.

14. The anticoagulant of claim 13, which is an antithrombotic agent.

15. A method of inhibiting activity and suppressing activation of thrombin in vivo which comprises administering to a mammal a pharmaceutically effective amount of a compound of claim 1.

* * * * *